United States Patent
Fouda et al.

(10) Patent No.: US 12,416,622 B2
(45) Date of Patent: Sep. 16, 2025

(54) SENSORS FOR MEASURING PROPERTIES OF MATERIALS FLOWING THROUGH A FLOWLINE

(71) Applicant: Halliburton Energy Services, Inc., Houston, TX (US)

(72) Inventors: Ahmed Fouda, Houston, TX (US); Baris Guner, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 229 days.

(21) Appl. No.: 18/081,914

(22) Filed: Dec. 15, 2022

(65) Prior Publication Data
US 2024/0201162 A1   Jun. 20, 2024

(51) Int. Cl.
*G01N 33/28* (2006.01)
*E21B 49/10* (2006.01)
*G01N 27/08* (2006.01)

(52) U.S. Cl.
CPC ......... *G01N 33/2823* (2013.01); *E21B 49/10* (2013.01); *G01N 27/08* (2013.01); *G01N 33/28* (2013.01)

(58) Field of Classification Search
CPC ....... E21B 49/081; E21B 49/10; G01N 27/08; G01N 33/28; G01N 33/2823
See application file for complete search history.

(56) References Cited

U.S. PATENT DOCUMENTS

| | | | |
|---|---|---|---|
| 5,677,631 A | 10/1997 | Reittinger et al. | |
| 6,938,470 B2 * | 9/2005 | DiFoggio | G01N 9/002 |
| | | | 73/152.16 |
| 7,574,898 B2 * | 8/2009 | Harrison | G01N 29/4418 |
| | | | 73/54.24 |
| 8,850,879 B2 * | 10/2014 | Swett | E21B 47/017 |
| | | | 73/152.24 |

(Continued)

FOREIGN PATENT DOCUMENTS

| | | |
|---|---|---|
| EP | 2104837 | 9/2017 |
| WO | 2016060860 | 4/2016 |

OTHER PUBLICATIONS

Balanis, Constantine A. "Antenna Theory Analysis and Design 3rd Edition. New Jersey: John Willey & Sons." Inc.[Jan. 3, 2020] (2005).

(Continued)

*Primary Examiner* — Jill E Culler
(74) *Attorney, Agent, or Firm* — Benjamin Ford; C. Tumey Law Group, PLLC

(57) ABSTRACT

A method and system for downhole sampling. The system may include a downhole fluid sampling tool that may include one or more probes configured to extend into a formation, and a pump configured to collect a fluid from the formation through the one or more probes. The method may further comprise a flowline configured to transport the fluid from the formation through the one or more probes and through the downhole fluid sampling tool and a fluid analysis module comprising a resonator antenna disposed on the (Continued)

flowline and configured to measure at least one property of the fluid. Additionally, the method may comprise measuring at least one property of the fluid with at least one resonator antennas that are disposed on or within an outer surface of the flowline.

20 Claims, 12 Drawing Sheets

(56) References Cited

U.S. PATENT DOCUMENTS

| | | | |
|---|---|---|---|
| 9,557,439 | B2 | 1/2017 | Wilson et al. |
| 9,562,864 | B2 * | 2/2017 | Harrison ................. H01P 7/06 |
| 10,101,492 | B2 | 10/2018 | Fouda et al. |
| 10,227,864 | B2 | 3/2019 | Donderici et al. |
| 10,241,226 | B2 | 3/2019 | Donderici et al. |
| 10,301,935 | B2 | 5/2019 | Wang et al. |
| 10,422,913 | B2 | 9/2019 | Fouda et al. |
| 10,520,638 | B1 | 12/2019 | Lowell et al. |
| 10,526,885 | B2 | 1/2020 | Fouda et al. |
| 10,591,628 | B2 | 3/2020 | Fouda et al. |
| 10,684,236 | B2 * | 6/2020 | Hurlimann ............. G01N 22/00 |
| 10,697,290 | B2 | 6/2020 | Wilson et al. |
| 11,377,946 | B2 | 7/2022 | Donderici et al. |
| 2014/0032116 | A1 | 1/2014 | Guner |
| 2014/0244175 | A1 | 8/2014 | Donderici et al. |
| 2014/0252250 | A1 | 9/2014 | Botto et al. |
| 2015/0309201 | A1 | 10/2015 | Wu et al. |
| 2016/0266271 | A1 | 9/2016 | Fouda et al. |
| 2017/0082770 | A1 | 3/2017 | Mandviwala et al. |
| 2017/0115236 | A1 | 4/2017 | Renlund et al. |
| 2017/0123096 | A1 | 5/2017 | Wilson et al. |
| 2017/0254917 | A1 | 9/2017 | Fouda et al. |
| 2018/0038222 | A1 | 2/2018 | Samson et al. |
| 2018/0283170 | A1 | 10/2018 | Donderici et al. |
| 2018/0329105 | A1 | 11/2018 | Capoglu et al. |
| 2019/0086575 | A1 | 3/2019 | Fouda et al. |
| 2019/0196039 | A1 | 6/2019 | Wilson et al. |
| 2019/0203580 | A1 | 7/2019 | Guner et al. |
| 2019/0218905 | A1 | 7/2019 | Donderici et al. |
| 2019/0353820 | A1 | 11/2019 | Chen et al. |
| 2020/0271817 | A1 | 8/2020 | Ewe et al. |
| 2020/0319362 | A1 | 10/2020 | Guner et al. |

OTHER PUBLICATIONS

Cheng, David Keun. Field and wave electromagnetics. Pearson New International Edition, 2014.
Fouda et al., U.S. Appl. No. 17/736,845 (unpublished), filed May 4, 2022.
Pfeiffer et al., Calibrated Formation Water Resistivity Sensor, May 2020.
Soeimani, Manuchehr, Super-sensing through industrial process tomography, Feb. 2016.
International Search Report and Written Opinion for International Patent Application No. PCT/US2023/010625 dated Sep. 5, 2023.

* cited by examiner

SENSORS FOR MEASURING PROPERTIES OF MATERIALS FLOWING THROUGH A FLOWLINE

BACKGROUND

Wells may be drilled at various depths to access and produce oil, gas, minerals, and other naturally-occurring deposits from subterranean geological formations. The drilling of a well is typically accomplished with a drill bit that is rotated within the well to advance the well by removing topsoil, sand, clay, limestone, calcites, dolomites, or other materials. During or after drilling operations, sampling operations may be performed to collect a representative sample of formation or reservoir fluids (e.g., hydrocarbons) to further evaluate drilling operations and production potential, or to detect the presence of certain gases or other materials in the formation that may affect well performance. Sampling operations may require the use of a downhole fluid sampling tool.

During sampling operations, a downhole fluid sampling tool may collect fluid samples from a formation. Generally, the fluid may flow through a flowline and undergo measurements. The fluid may then be removed from the fluid sampling tool into a wellbore or saved as a fluid sample within the downhole fluid sampling tool. During such sampling operations, it may be valuable to perform resistivity and permittivity measurements on the fluid flowing through the flowline. In examples, logging may be performed directly on a production flowline without the physical sampling of the fluid as well. In further examples, resistivity and permittivity measurements may be utilized to determine the properties of the fluid and/or materials within the fluid passing through the flowline and/or quantify the changes in flow over time.

Electrodes have traditionally been utilized as antennas in flowlines to determine the resistivity of the fluid passing through. However, electrodes tend to be easily coated by particles in the fluid flowing through the flowline, such as a small film of oil or dissolved minerals inside the fluid. As a result, resistivity measurements with electrodes may yield bias in the resulting resistivity measurements, affecting the accuracy of the petrophysical estimates. Furthermore, electrodes work on galvanic principles, thus requiring the continuous phase in the fluid to be conductive. Coil antennas may also be used to determine resistivity and permittivity measurements to determine the properties of the fluid and/or materials within the fluid passing through the flowline and/or quantify the changes in flow over time. However, coil antennas employ induction principles and the received signal is proportional to the conductivity of the materials in the volume of sensitivity of the tool. Thus, they do not work in the presence of conducting or magnetic flowlines. Additionally, a high-frequency flowline antenna design that is capable of measuring both the conductivity and the permittivity of the fluid requires a purpose-built flowline design. Currently, technology is not able to provide an antenna structure for traditional flowlines that does not degrade over time due to the accumulation of contaminants from the fluids and capable of making measurements in conducting flowlines.

BRIEF DESCRIPTION OF THE DRAWINGS

These drawings illustrate certain aspects of some examples of the present disclosure and should not be used to limit or define the disclosure.

DETAILED DESCRIPTION

The present disclosure relates to methods and systems for measuring resistivity and permittivity measurements to determine the properties of a fluid passing through the flowline and/or quantify the changes in flow over time. Specifically, resonator antennas may perform resistivity and permittivity measurements in flowlines of a downhole fluid sampling tool or directly in flowlines of the production tubing. Resonator antennas may not be affected by the accumulation of particles and may measure both conductive and nonconductive fluid. Furthermore, resonator antennas may be low-profile, easy to manufacture, have a high signal-to-noise ratio, and low leakage. Discussed below are methods and systems for measuring properties of material and fluids within a flowline. Although the rest of the discussion will focus on the flowlines of a downhole fluid sampling tool, same methods and systems may also be used in the flowlines of production tubing that does not perform fluid sampling without any loss of generality. Additionally, methods and systems may comprise tomography designs that may be capable of measuring the phases of the material and fluids within the downhole fluid sampling tool.

Figure 1:
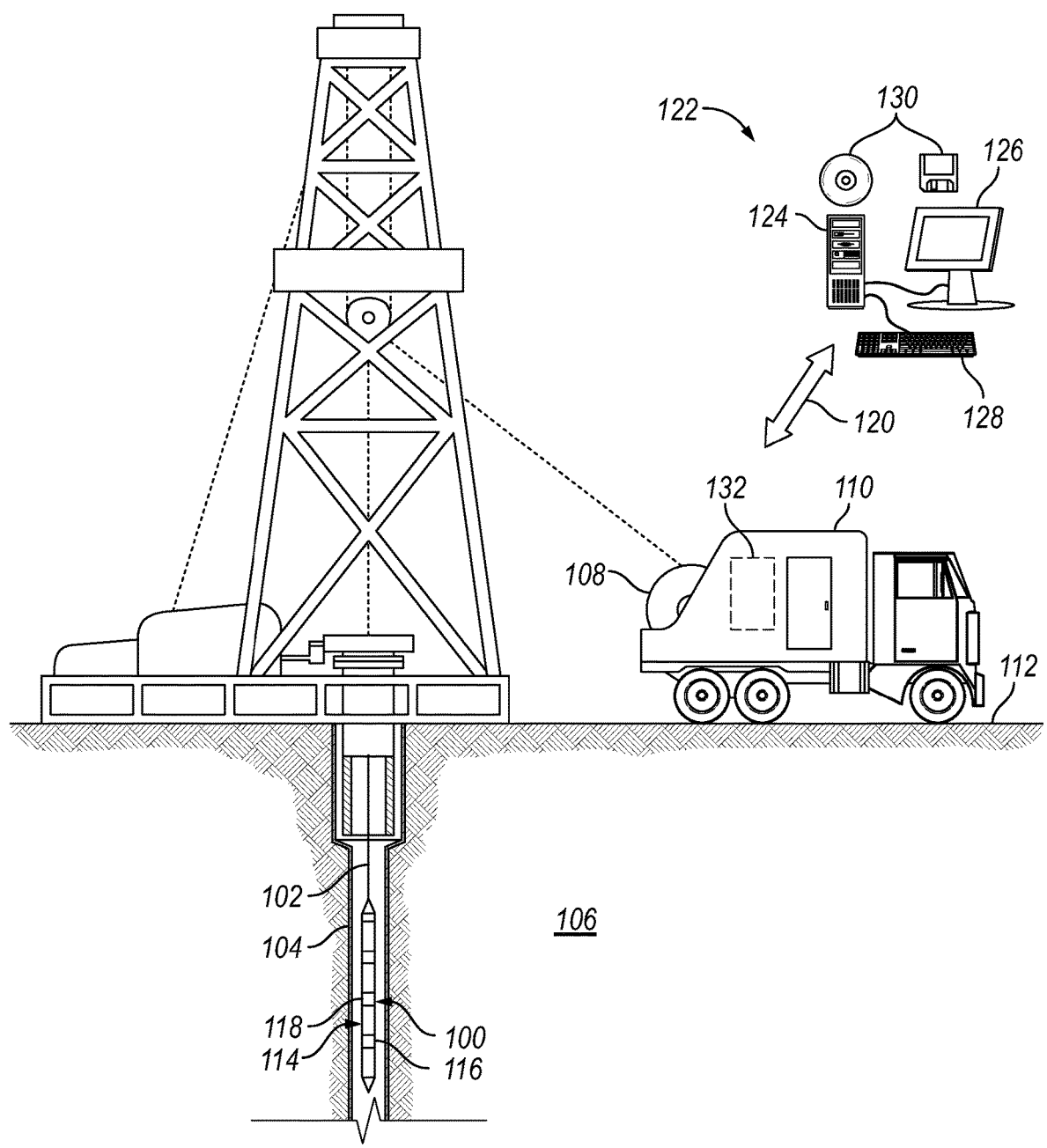
FIG. 1 illustrates a schematic view of a well in which an example embodiment of a fluid sample system is deployed.

FIG. 1 is a schematic diagram of downhole fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole fluid sampling tool 100 may be suspended in wellbore 104 on conveyance 102. Other conveyance types may be used for conveying downhole fluid sampling tool 100 into wellbore 104, including coiled tubing and wired drill pipe, for example, Downhole fluid sampling tool 100 may comprise a tool body 114, which may be elongated as shown on FIG. 1. Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 104, subterranean formation 106, or the like. In examples, downhole fluid sampling tool 100 may also include a fluid analysis module 118, which may be operable to process information regarding fluid sample, as described below. The downhole fluid sampling tool 100 may be used to collect fluid samples from subterranean formation 106 and may obtain and separately store different fluid samples from subterranean formation 106. In examples, fluid analysis module 118 may comprise at least one resonator antenna 160. Resonator antenna 160 may form more than one configuration, described in detail in FIGS. 7A, 7B, 8, 9, 10A, 10B, 10C, 11A, 11B, 13A, 13B, and 13C. Resonator antenna 160 may be configured to measure S parameters of fluids within sampling tool 100, to be described in detail below.

Any suitable technique may be used for transmitting signals from the downhole fluid sampling tool 100 to the surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. Information handling system 122 may act as a data acquisition system and possibly a data processing system that analyzes information from downhole fluid sampling tool 100. For example, information handling system 122 may process the information from downhole fluid sampling tool 100 for determination of fluid contamination. The information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of downhole fluid sampling tool 100 from wellbore 104. Alternatively, the processing may be performed by an information handling system in wellbore 104, such as fluid analysis module 118. The resultant fluid contamination and fluid properties may then be transmitted to surface 112, for example, in real-time. Real time may be defined within any range comprising 0.01 seconds to 0.1 seconds, 0.1 seconds to 1 second, 1 second to 1 minute, 1 minute to 1 hour, 1 hour to 4 hours, or any combination of ranges provided.

Figure 2:
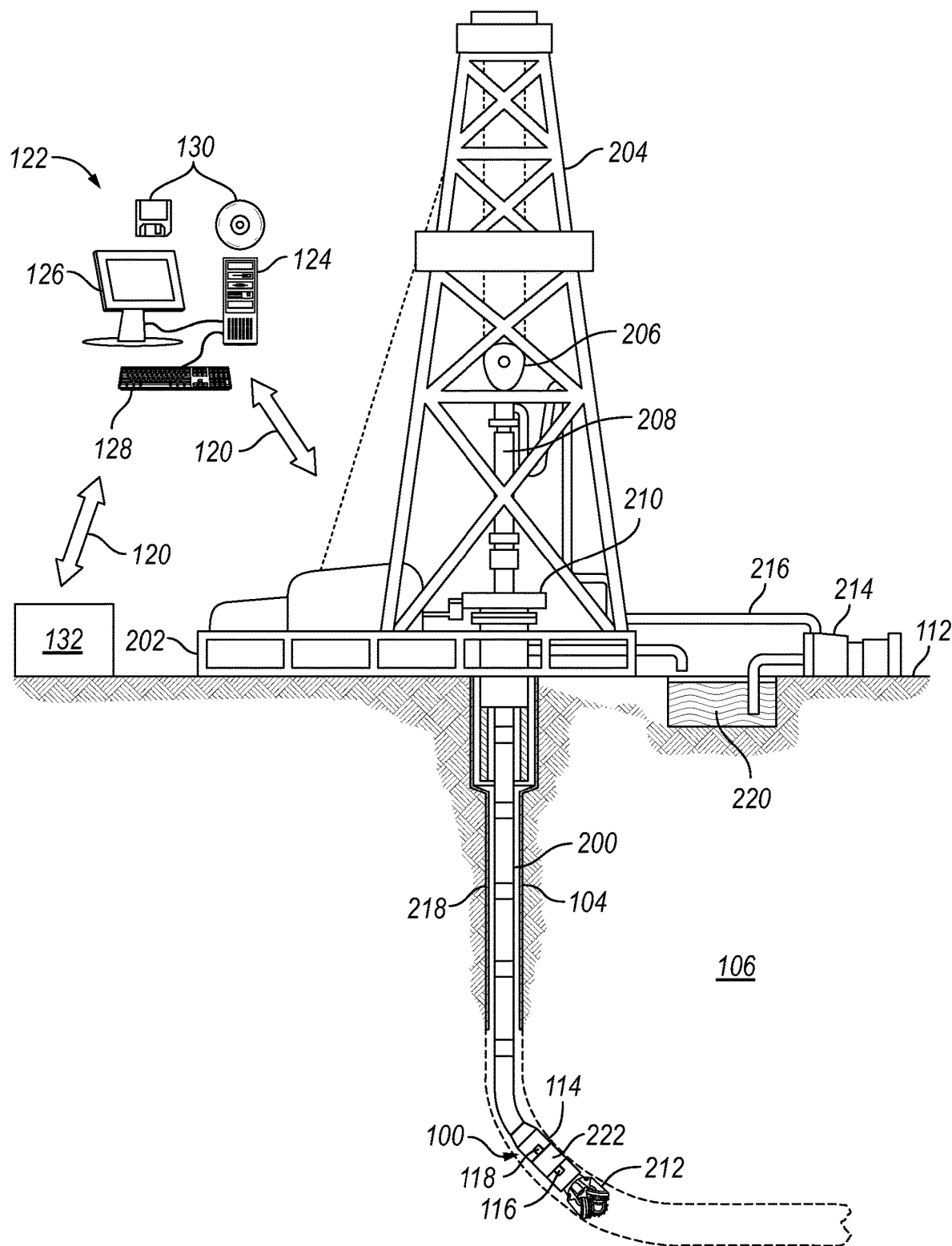
FIG. 2 illustrates a schematic view of another well in which an example embodiment of a fluid sample system is deployed.

Referring now to FIG. 2, a schematic diagram of downhole fluid sampling tool 100 disposed on a drill string 200 in a drilling operation. Downhole fluid sampling tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole fluid sampling tool 100. Downhole fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole fluid sampling tool 100 may be similar in configuration and operation to downhole fluid sampling tool 100 shown on FIG. 1 except that FIG. 2 shows downhole fluid sampling tool 100 disposed on drill string 200. Alternatively downhole fluid sampling tool 100 may be lowered into the wellbore after drilling operations on a wireline.

Downhole fluid sampling tool 100 may further include one or more sensors 116 for measuring properties of the fluid sample reservoir fluid, wellbore 104, subterranean formation 106, or the like. The one or more sensors 116 may be disposed within fluid analysis module 118. In examples, more than one fluid analysis module may be disposed on drill string 200. The properties of the fluid are measured as the fluid passes from the formation through downhole fluid sampling tool 100 and into either the wellbore or a sample container. As fluid is flushed in the near wellbore region by the mechanical pump, the fluid that passes through downhole fluid sampling tool 100 generally reduces in drilling fluid filtrate content, and generally increases in formation fluid content. The downhole fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low may also depend on the rate of cleanup in a cost benefit analysis since longer pumpout times required to incrementally reduce the contamination levels may have prohibitively large costs. As previously described, the fluid sample may comprise a reservoir fluid, which may be contaminated with a drilling fluid or drilling fluid filtrate. Downhole fluid sampling tool 100 may obtain and separately store different fluid samples from subterranean formation 106 with fluid analysis module 118. Fluid analysis module 118 may operate and function in the same manner as described above. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100. In examples, contamination may be defined within fluid analysis module 118.

As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate electromagnetic properties of a fluid sample.

Figure 3:
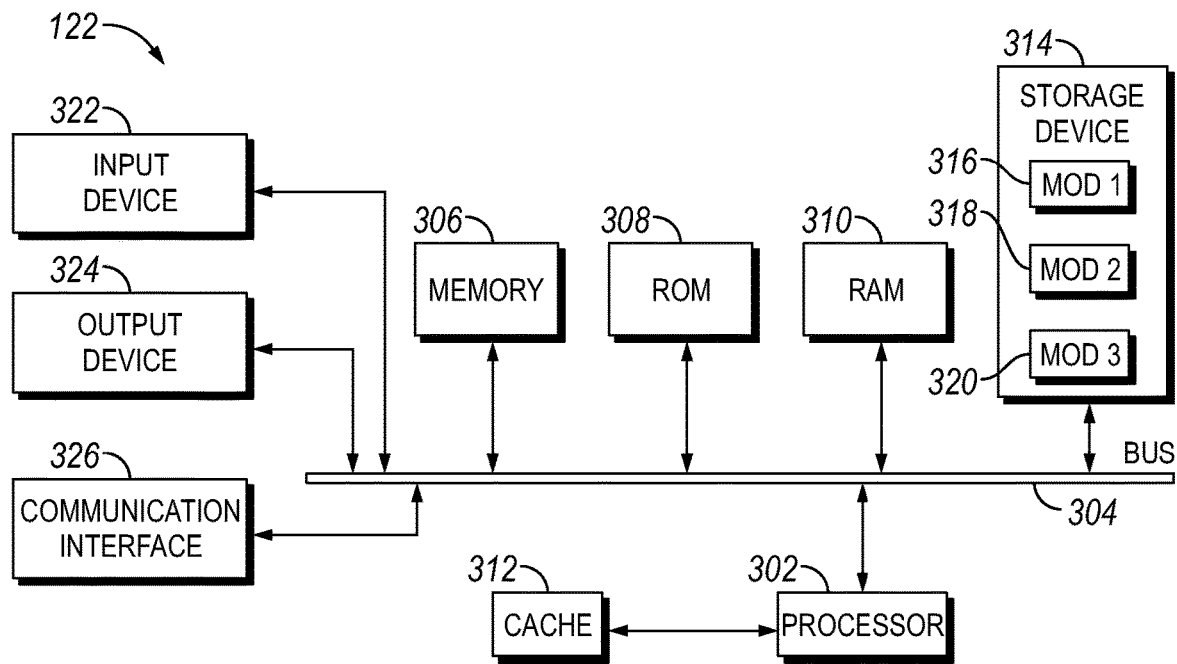
FIG. 3 illustrates a schematic view of a chipset in an information handling system.

FIG. 3 illustrates an example information handling system 122 which may be employed to perform various steps, methods, and techniques disclosed herein. As illustrated, information handling system 122 includes a processing unit (CPU or processor) 302 and a system bus 304 that couples various system components including system memory 306 such as read only memory (ROM) 308 and random-access memory (RAM) 310 to processor 302. Processors disclosed herein may all be forms of this processor 302. Information handling system 122 may include a cache 312 of high-speed memory connected directly with, in close proximity to, or integrated as part of processor 302. Information handling system 122 copies data from memory 306 and/or storage device 314 to cache 312 for quick access by processor 302. In this way, cache 312 provides a performance boost that avoids processor 302 delays while waiting for data. These and other modules may control or be configured to control processor 302 to perform various operations or actions. Other system memory 306 may be available for use as well. Memory 306 may include multiple different types of memory with different performance characteristics. It may be appreciated that the disclosure may operate on information handling system 122 with more than one processor 302 or on a group or cluster of computing devices networked together to provide greater processing capability. Processor 302 may include any general purpose processor and a hardware module or software module, such as first module 316, second module 318, and third module 320 stored in storage device 314, configured to control processor 302 as well as a special-purpose processor where software instructions are incorporated into processor 302. Processor 302 may be a self-contained computing system, containing multiple cores or processors, a bus, memory controller, cache, etc. A multi-core processor may be symmetric or asymmetric. Processor 302 may include multiple processors, such as a system having multiple, physically separate processors in different sockets, or a system having multiple processor cores on a single physical chip. Similarly, processor 302 may include multiple distributed processors located in multiple separate computing devices but working together such as via a communications network. Multiple processors or processor cores may share resources such as memory 306 or cache 312 or may operate using independent resources. Processor 302 may include one or more state machines, an application specific integrated circuit (ASIC), or a programmable gate array (PGA) including a field PGA (FPGA).

Each individual component discussed above may be coupled to system bus 304, which may connect each and every individual component to each other. System bus 304 may be any of several types of bus structures including a memory bus or memory controller, a peripheral bus, and a local bus using any of a variety of bus architectures. A basic input/output (BIOS) stored in ROM 308 or the like, may provide the basic routine that helps to transfer information between elements within information handling system 122, such as during start-up. Information handling system 122 further includes storage devices 314 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. Storage device 314 may include software modules 316, 318, and 320 for controlling processor 302. Information handling system 122 may include other hardware or software modules. Storage device 314 is connected to the system bus 304 by a drive interface. The drives and the associated computer-readable storage devices provide nonvolatile storage of computer-readable instructions, data structures, program modules and other data for information handling system 122. In one aspect, a hardware module that performs a particular function includes the software component stored in a tangible computer-readable storage device in connection with the necessary hardware components, such as processor 302, system bus 304, and so forth, to carry out a particular function. In another aspect, the system may use a processor and computer-readable storage device to store instructions which, when executed by the processor, cause the processor to perform operations, a method or other specific actions. The basic components and appropriate variations may be modified depending on the type of device, such as whether information handling system 122 is a small, handheld computing device, a desktop computer, or a computer server. When processor 302 executes instructions to perform "operations", processor 302 may perform the operations directly and/or facilitate, direct, or cooperate with another device or component to perform the operations.

As illustrated, information handling system 122 employs storage device 314, which may be a hard disk or other types of computer-readable storage devices which may store data that are accessible by a computer, such as magnetic cassettes, flash memory cards, digital versatile disks (DVDs), cartridges, random access memories (RAMs) 310, read only memory (ROM) 308, a cable containing a bit stream and the like, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with information handling system 122, an input device 322 represents any number of input mechanisms, such as a microphone for speech, a touch-sensitive screen for gesture or graphical input, keyboard, mouse, motion input, speech and so forth. Additionally, input device 322 may take in data from one or more sensors 136, discussed above. An output device 324 may also be one or more of a number of output mechanisms known to those of skill in the art. In some instances, multimodal systems enable a user to provide multiple types of input to communicate with information handling system 122. Communications interface 326 generally governs and manages the user input and system output. There is no restriction on operating on any particular hardware arrangement and therefore the basic hardware depicted may easily be substituted for improved hardware or firmware arrangements as they are developed.

As illustrated, each individual component describe above is depicted and disclosed as individual functional blocks. The functions these blocks represent may be provided through the use of either shared or dedicated hardware, including, but not limited to, hardware capable of executing software and hardware, such as a processor 302, that is purpose-built to operate as an equivalent to software executing on a general purpose processor. For example, the functions of one or more processors presented in FIG. 3 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 308 for storing software performing the operations described below, and random-access memory (RAM) 310 for storing results. Very large-scale integration (VLSI) hardware embodiments, as well as custom VLSI circuitry in combination with a general-purpose DSP circuit, may also be provided.

The logical operations of the various methods, described below, are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. Information handling system 122 may practice all or part of the recited methods, may be a part of the recited systems, and/or may operate according to instructions in the recited tangible computer-readable storage devices. Such logical operations may be implemented as modules configured to control processor 302 to perform particular functions according to the programming of software modules 316, 318, and 320.

In examples, one or more parts of the example information handling system 122, up to and including the entire information handling system 122, may be virtualized. For example, a virtual processor may be a software object that executes according to a particular instruction set, even when a physical processor of the same type as the virtual processor is unavailable. A virtualization layer or a virtual "host" may enable virtualized components of one or more different computing devices or device types by translating virtualized operations to actual operations. Ultimately however, virtualized hardware of every type is implemented or executed by some underlying physical hardware. Thus, a virtualization compute layer may operate on top of a physical compute layer. The virtualization compute layer may include one or more virtual machines, an overlay network, a hypervisor, virtual switching, and any other virtualization application.

Figure 4:
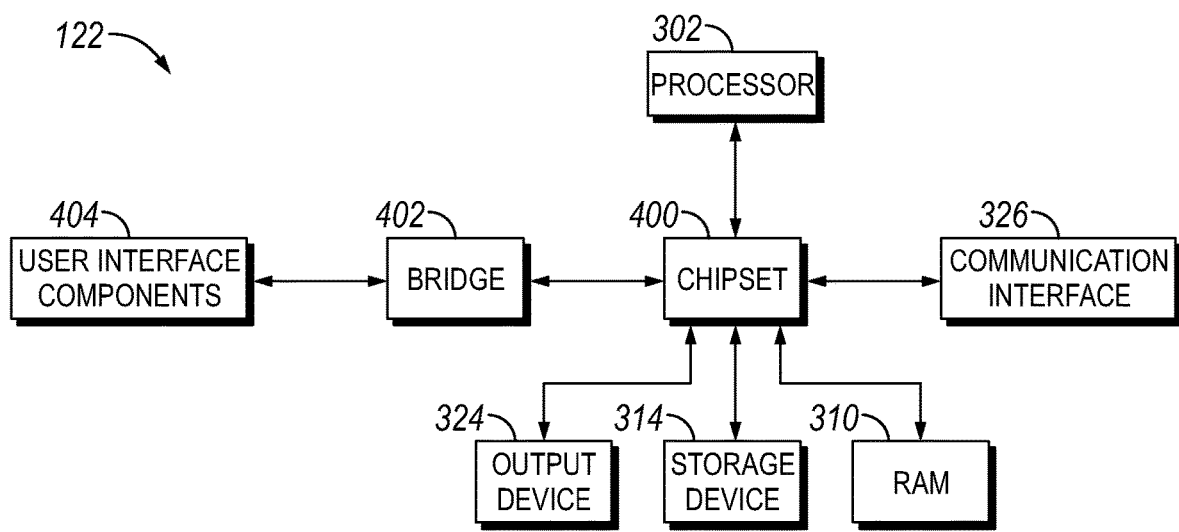
FIG. 4 illustrates the chipset in communication with other components of the information handling system.

FIG. 4 illustrates an example information handling system 122 having a chipset architecture that may be used in executing the described method and generating and displaying a graphical user interface (GUI). Information handling system 122 is an example of computer hardware, software, and firmware that may be used to implement the disclosed technology. Information handling system 122 may include a processor 302, representative of any number of physically and/or logically distinct resources capable of executing software, firmware, and hardware configured to perform identified computations. Processor 302 may communicate with a chipset 400 that may control input to and output from processor 302. In this example, chipset 400 outputs information to output device 324, such as a display, and may read and write information to storage device 314, which may include, for example, magnetic media, and solid-state media. Chipset 400 may also read data from and write data to RAM 310. A bridge 402 for interfacing with a variety of user interface components 404 may be provided for interfacing with chipset 400. Such user interface components 404 may include a keyboard, a microphone, touch detection and processing circuitry, a pointing device, such as a mouse, and so on. In general, inputs to information handling system 122 may come from any of a variety of sources, machine generated and/or human generated.

Chipset 400 may also interface with one or more communication interfaces 326 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 302 analyzing data stored in storage device 314 or RAM 310. Further, information handling system 122 receive inputs from a user via user interface components 404 and execute appropriate functions, such as browsing functions by interpreting these inputs using processor 302.

In examples, information handling system 122 may also include tangible and/or non-transitory computer-readable storage devices for carrying or having computer-executable instructions or data structures stored thereon. Such tangible computer-readable storage devices may be any available device that may be accessed by a general purpose or special purpose computer, including the functional design of any special purpose processor as described above. By way of example, and not limitation, such tangible computer-readable devices may include RAM, ROM, EEPROM, CD-ROM or other optical disk storage, magnetic disk storage or other magnetic storage devices, or any other device which may be used to carry or store desired program code in the form of computer-executable instructions, data structures, or processor chip design. When information or instructions are provided via a network, or another communications connection (either hardwired, wireless, or combination thereof), to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

In additional examples, methods may be practiced in network computing environments with many types of computer system configurations, including personal computers, hand-held devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 5:
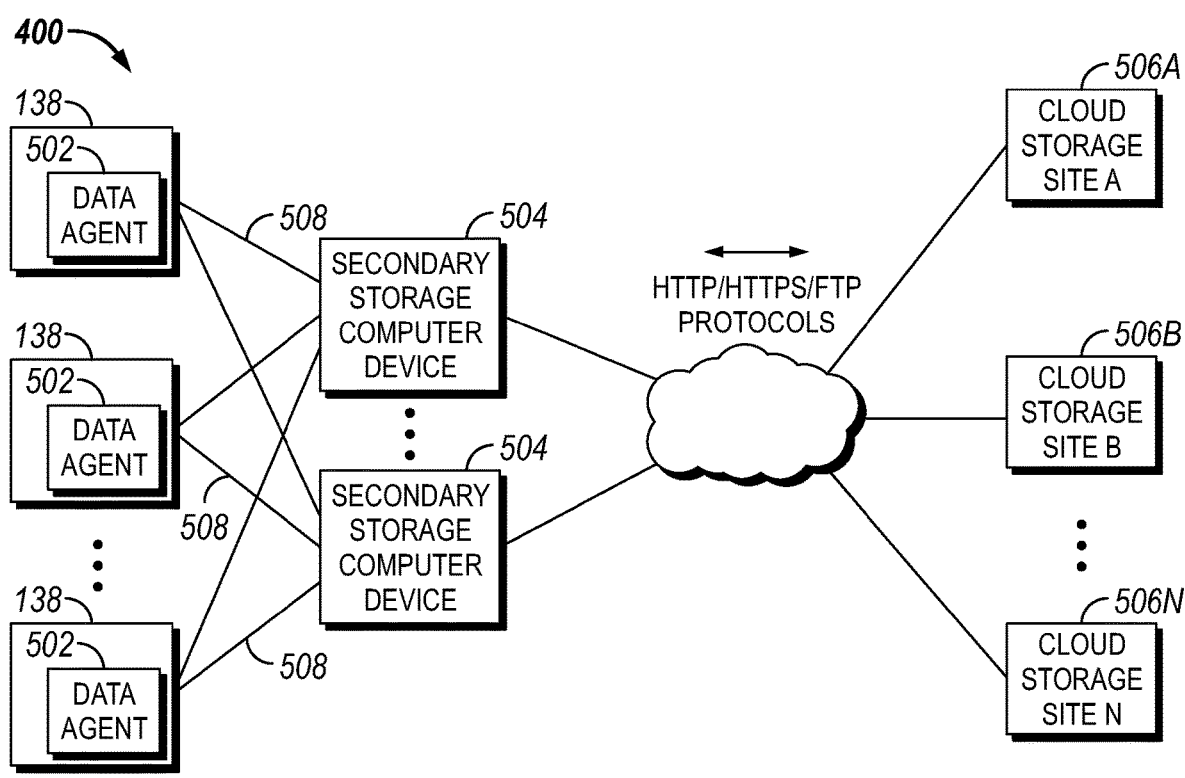
FIG. 5 illustrates an example of one arrangement of resources in a computing network.

FIG. 5 illustrates an example of one arrangement of resources in a computing network 500 that may employ the processes and techniques described herein, although many others are of course possible. As noted above, an information handling system 122, as part of their function, may utilize data, which includes files, directories, metadata (e.g., access control list (ACLS) creation/edit dates associated with the data, etc.), and other data objects. The data on the information handling system 122 is typically a primary copy (e.g., a production copy). During a copy, backup, archive or other storage operation, information handling system 122 may send a copy of some data objects (or some components thereof) to a secondary storage computing device 504 by utilizing one or more data agents 502.

A data agent 502 may be a desktop application, website application, or any software-based application that is run on information handling system 122. As illustrated, information handling system 122 may be disposed at any rig site (e.g., referring to FIG. 1) or repair and manufacturing center. Data agent 502 may communicate with a secondary storage computing device 504 using communication protocol 508 in a wired or wireless system. Communication protocol 508 may function and operate as an input to a website application. In the website application, field data related to pre- and post-operations, generated DTCs, notes, and the like may be uploaded. Additionally, information handling system 122 may utilize communication protocol 508 to access processed measurements, operations with similar DTCs, troubleshooting findings, historical run data, and/or the like. This information is accessed from secondary storage computing device 504 by data agent 502, which is loaded on information handling system 122.

Secondary storage computing device 504 may operate and function to create secondary copies of primary data objects (or some components thereof) in various cloud storage sites 506A-N. Additionally, secondary storage computing device 504 may run determinative algorithms on data uploaded from one or more information handling systems 138, discussed further below. Communications between the secondary storage computing devices 504 and cloud storage sites 506A-N may utilize REST protocols (Representational state transfer interfaces) that satisfy basic C/R/U/D semantics (Create/Read/Update/Delete semantics), or other hypertext transfer protocol ("HTTP")-based or file-transfer protocol ("FTP")-based protocols (e.g., Simple Object Access Protocol).

In conjunction with creating secondary copies in cloud storage sites 506A-N, the secondary storage computing device 504 may also perform local content indexing and/or local object-level, sub-object-level or block-level deduplication when performing storage operations involving various cloud storage sites 506A-N. Cloud storage sites 506A-N may further record and maintain DTC code logs for each downhole operation or run, map DTC codes, store repair and maintenance data, store operational data, and/or provide outputs from determinative algorithms that are fun at cloud storage sites 506A-N. In examples, computing network 500 may be communicatively coupled to downhole fluid sampling tool 100.

Figure 6:
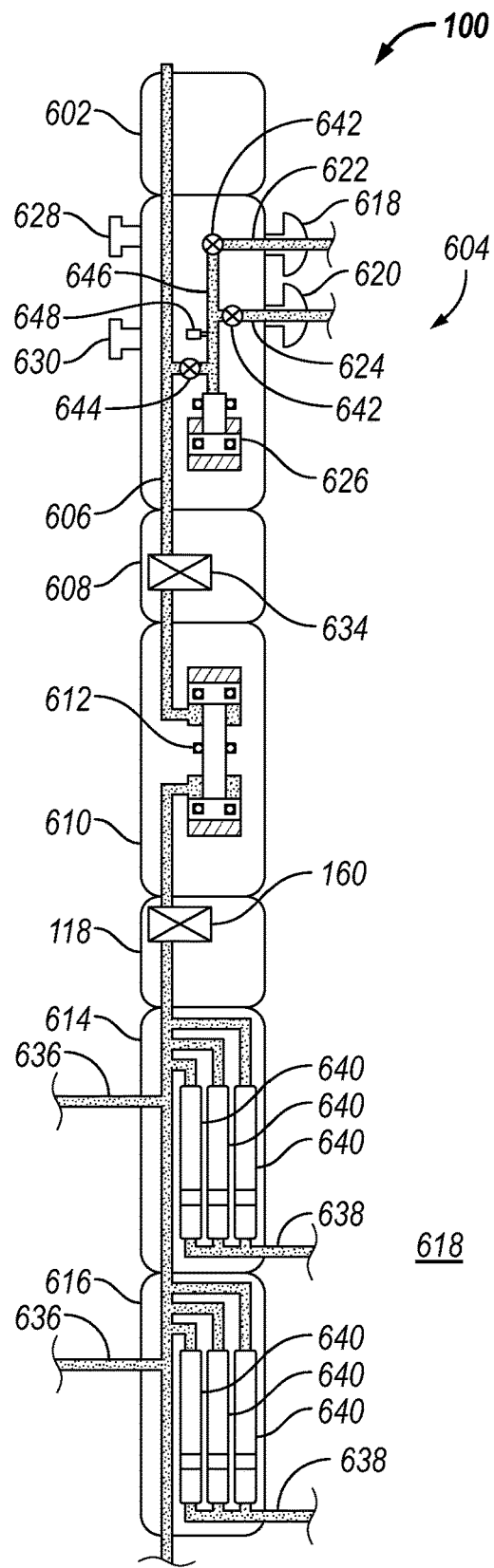
FIG. 6 illustrates a schematic view of an example embodiment of a fluid sampling tool.

FIG. 6 illustrates a schematic of downhole fluid sampling tool 100. As illustrated, downhole fluid sampling tool 100 may comprise probe 604. Probe 604 may extract fluid from the reservoir and deliver it to a flowline 606 that extends from one end of downhole fluid sampling tool 100 to the other. Without limitation, probe 604 includes two probes 618, 620 which may extend from downhole fluid sampling tool 100 and press against the inner wall of wellbore 104 (e.g., referring to FIG. 1). Probe channels 622, 624 may connect probes 618, 620 to flowline 606. The high-volume bidirectional pump 612 may be used to pump fluids from the reservoir, through probe channels 622, 624 and to flowline 606. Alternatively, a low volume pump 626 may be used for this purpose. Two standoffs or stabilizers 628, 630 hold downhole fluid sampling tool 100 in place as probes 618, 620 press against the wall of wellbore 104. In examples, probes 618, 620 and stabilizers 628, 630 may be retracted when downhole fluid sampling tool 100 may be in motion and probes 618, 620 and stabilizers 628, 630 may be extended to sample the reservoir fluids at any suitable location in wellbore 104.

In examples, flowline 606 may be connected to other tools disposed on drill string 200 or conveyance 102 (e.g., referring to FIGS. 1 and 2). Additionally, downhole fluid sampling tool 100 may include a flow-control pump-out section 610, which may include a high-volume bidirectional pump 612 for pumping fluid through flowline 606. In examples, downhole fluid sampling tool 100 may include two multi-chamber sections 614, 616, referred to collectively as multi-chamber sections 614, 616 or individually as first multi-chamber section 614 and second multi-chamber section 616, respectively.

In examples, multi-chamber sections 614, 616 may be separated from flow-control pump-out section 610 by sensor section 632, which may house one or more sensors 634. Sensor 634 may be displaced within sensor section 632 in-line with flowline 606 to be a "flow through" sensor. In alternate examples, sensor 634 may be connected to flowline 606 via an offshoot of flowline 606. Without limitation, sensor 634 may include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, sensor 634 may operate and/or function to measure drilling fluid filtrate.

Additionally, multi-chamber section 614, 616 may comprise access channel 636 and chamber access channel 638. Without limitation, access channel 636 and chamber access channel 638 may operate and function to either allow a solids-containing fluid (e.g., mud) disposed in wellbore 104 in or provide a path for removing fluid from downhole fluid sampling tool 100 into wellbore 104. As illustrated, multi-chamber section 614, 616 may comprise a plurality of chambers 640). Chambers 640 may be sampling chamber that may be used to sample wellbore fluids, reservoir fluids, and/or the like during measurement operations. It should be noted that downhole fluid sampling tool 100 may also be used in pressure testing operations.

For example, during pressure testing operations, probes 618, 620 may be pressed against the inner wall of wellbore 104 (e.g., referring to FIG. 1). Pressure may increase at probes 618, 620 due to formation 106 (e.g., referring to FIG. 1 or 2) exerting pressure on probes 618, 620. As pressure rises and reaches a predetermined pressure, valves 642 opens so as to close equalizer valve 644, thereby isolating fluid passageway 646 from the annulus 218. In this manner, valve 642 ensures that equalizer valve 644 closes only after probes 618, 620 has entered contact with mudcake (not illustrated) that is disposed against the inner wall of wellbore 104. In examples, as probes 618, 620 are pressed against the inner wall of wellbore 104, the pressure rises and closes the equalizer valve in fluid passageway 646, thereby isolating the fluid passageway 646 from the annulus 218. In this manner, the equalizer valve in fluid passageway 646 may close before probes 618, 620 may have entered contact with the mudcake that lines the inner wall of wellbore 104. Fluid passageway 646, now closed to annulus 218 (e.g., referring to FIG. 2), is in fluid communication with low volume pump 626.

As low volume pump 626 is actuated, formation fluid may thus be drawn through probe channels 622, 624 and probes 618, 620. The movement of low volume pump 626 lowers the pressure in fluid passageway 646 to a pressure below the formation pressure, such that formation fluid is drawn through probe channels 622, 624 and probes 618, 620 and into fluid passageway 646. The pressure of the formation fluid may be measured in fluid passageway 646 while probes 618, 620 serves as a seal to prevent annular fluids from entering fluid passageway 646 and invalidating the formation pressure measurement.

With low volume pump 626 in its fully retracted position and formation fluid drawn into fluid passageway 646, the pressure will stabilize and enable pressure transducers 648 to sense and measure formation fluid pressure. The measured pressure is transmitted to information handling system 122 disposed on downhole fluid sampling tool 100 and/or it may be transmitted to the surface via mud pulse telemetry or by any other conventional telemetry means to an information handling system 122 disposed on surface 112. Additionally, flowline 606 may pass through fluid analysis module 118 which may comprise at least one resonator antenna 160. In examples, fluid analysis module 118 may be disposed at any location within downhole sampling tool 100. Additionally, one or more fluid analysis module 118 with at least one resonator antenna 160 to perform resistivity analysis on fluid within flowline 606. However, further implementations to measure fluid within flowline 606 may be performed.

Figure 7A:
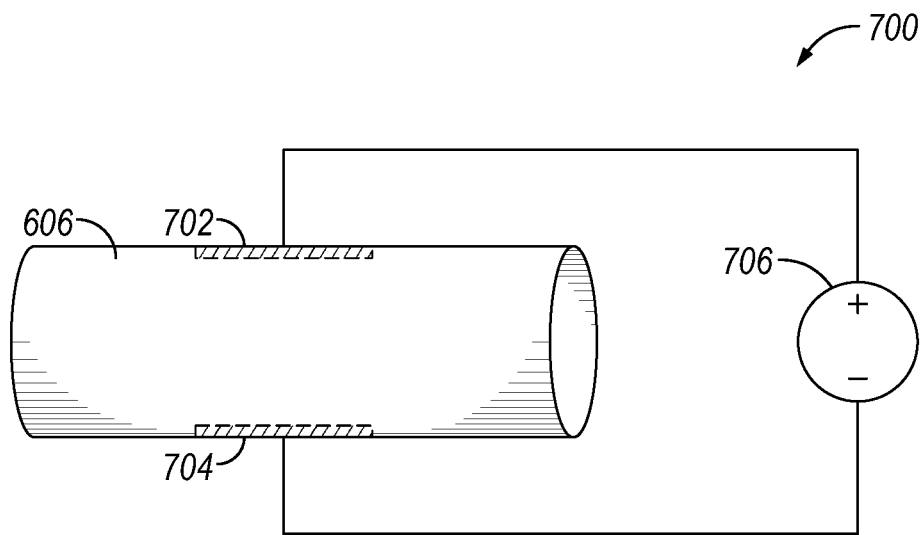
FIG. 7A illustrates an electrode system.

For example, FIG. 7A illustrates an electrode system 700 to measure resistivity in flowline 606. In electrode system 700, current may be transmitted through transmitter electrode 702 and returned to return electrode 704. As such, current may travel through the fluid inside flowline 606. Herein, fluid inside flowline 606 may contain material of any phase but is strictly referred to as fluid inside flowline 606. Electrode system 700 may operate with a DC Voltage Source 706. The potential drop between transmitter electrode 702 and the return electrode 704 may be a measure of the resistivity of this material in such static conditions. In examples, if the fluid is not homogeneous (i.e., single-phase), the resulting measurement may be representative of the average resistivity of the fluid. Additionally, although the term fluid is commonly used in practice, material flowing through the flowline may include gas or solid components. In examples where an alternating current is applied between transmitter electrode 702 and return electrode 704, a complex impedance may be measured where the measurement is influenced by the permittivity of the material (to be discussed below). However, in quasi-static conditions where the frequency is low (for example, less than 100 kHz), imaginary part of the measured impedance and effect of the permittivity may be ignored.

Electrode system 700 may operate on Galvanic principles and requires a physical contact between both transmitter and return electrodes 702 and 704 to the fluid inside flowline 606. Thus, electrode system 700 may be invasive for both transmitter and return electrodes 702 and 704. As such, corrosion on transmitter and return electrodes 702 and 704 may occur since they are directly exposed to the fluid inside flowline 606. Further, electrode system 700 may also require a flowline 606 to be non-conductive such that current will not be short-circuited through the outer surface of flowline 606. If the fluid inside flowline 606 is non-conductive, current will not readily flow thus the primary applications of such a sensor system in oil-field applications is to measure the salinity of the formation water. In a similar design, a pair of capacitor plates may be used to determine the capacitance of the fluid inside flowline 606. As with the electrode sensors shown in FIG. 7A, if the fluid is not homogeneous and include multiple phases, measurement will represent the average capacitance of the fluid. Setup for the capacitance sensors may be the same as the one shown in Error! Reference source not found. FIG. 7A for the electrode sensors. The fluid in this case should have low conductivity; otherwise, a conduction current may occur, and no charge will accumulate on the capacitor plates. In addition to electrodes measuring the properties of fluid within flowline 606, coil antennas may be used as well.

Figure 7B:
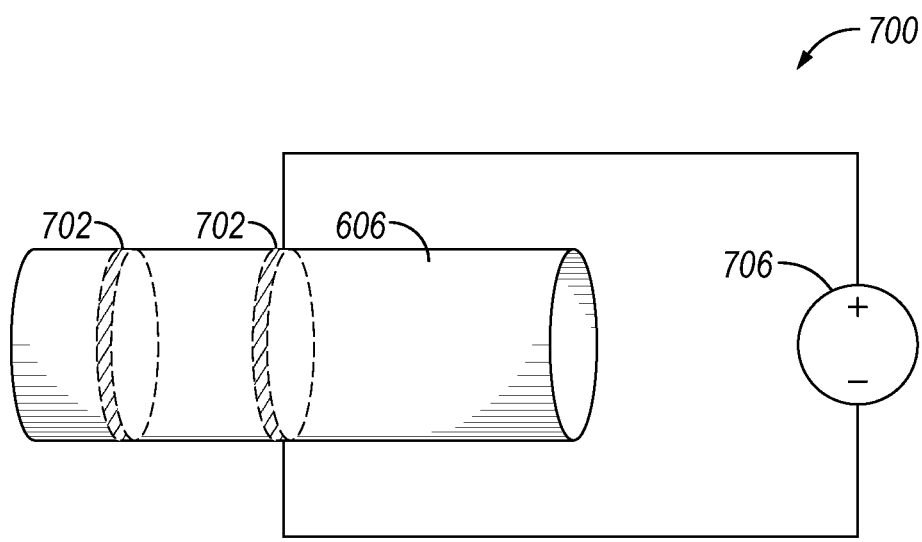
FIG. 7B illustrates a coil antenna system.

FIG. 7B illustrates coil antenna system 710, a low-frequency AC current source 716 may be passed through a transmitting coil antenna 712. The frequency if the AC current source may range between 1 kHz to 1 MHz. Current within transmitting coil antenna 712 forms a magnetic field in the direction perpendicular to the plane of transmitting coil antenna 712. The alternating magnetic field creates an induced electric field inside the flowline 606. This induced electric field in turn creates a secondary magnetic field at receiving coil antenna 714. The secondary magnetic field may be measured by receiving coil antenna 714. The secondary magnetic field measured by receiving coil antenna 714 may be in proportion to the conductivities within the volume of investigation of the tool. Since the volume of investigation is not restricted to the inside of the flowline, this type of sensors will be more sensitive to conductive fluids (that is, in a given environment, more conductive the fluid, more of the measured signal would be coming from the fluid); thus, they are primarily used to measure the salinity of the formation water as well and they may not operate in conducting or magnetic flowlines. In addition to electrode and coil systems, waveguide flowline sensors may be implemented.

Figure 7C:
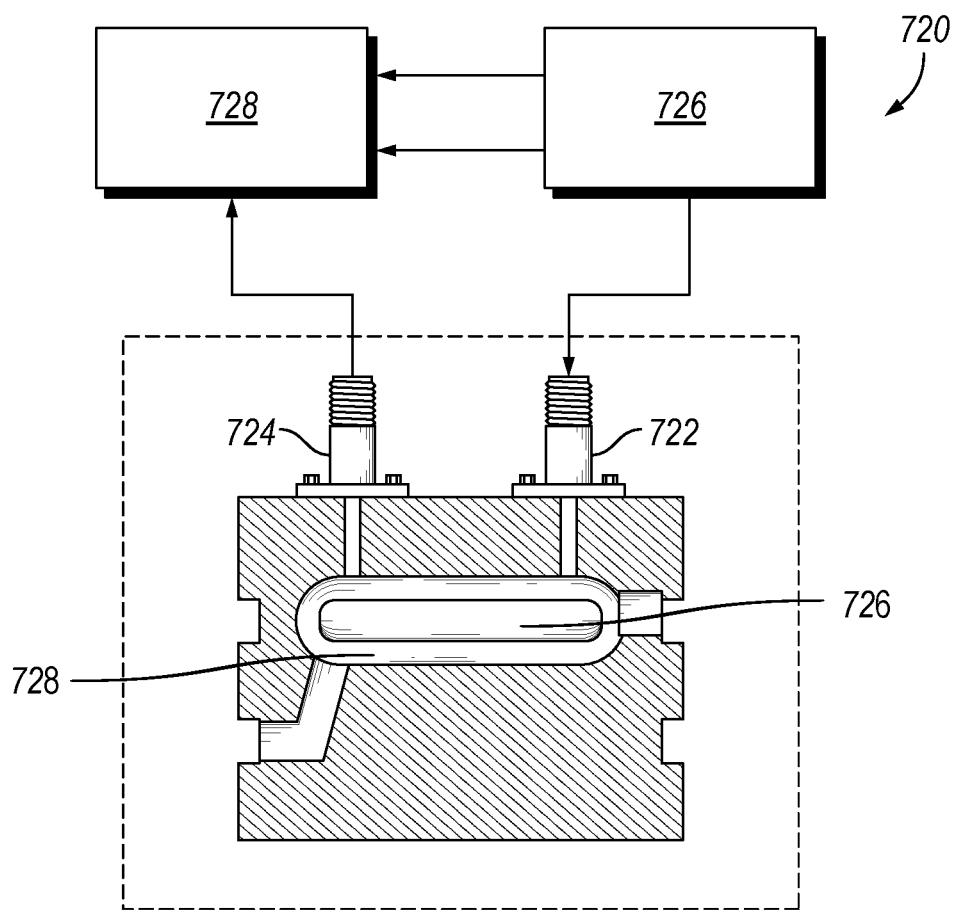
FIG. 7C illustrates a waveguide flowline sensor.

FIG. 7C illustrates waveguide flowline sensor 720. Waveguide flowline sensor 720 may measure fluid conductivity and permittivity. Thus, it may be used to determine the components of the fluid (e.g., oil/water ratio.) In examples, waveguide flowline sensor 720 may operate at 100 MHz. Waveguide flowline sensor 720 may comprise a coaxial conductor input 722 and a coaxial conductor output 724. Coaxial conductor input 722 may serve as a connection between waveguide flowline sensor 720 and conductor input 722. Similarly, coaxial conductor output 724 may serve as a connection between waveguide flowline sensor 720 and coaxial conductor output 724. Both the coaxial conductor input 724 and the coaxial conductor input are connected a central conductor 726 within the walls of the flowline cavity 728. As a result, central conductor 726 and the walls of the flowline cavity 728 forms a waveguide. The characteristic impedance of the waveguide is changed with the electrical properties of the fluid flowing through the flowline which enables the determination of such properties. Waveguide flowline sensor 720 may require a purpose-built flowline cavity 728 with central conductor 726. As such, waveguide flowline sensor 720 may not be adapted to work with existing flowlines. As previously discussed, multiple materials (i.e., multiphase flow) may flow through flowline 606 at the same time. For example, water, oil and gas may flow through flowline 606. In multiphase flow, measurements from waveguide flowline sensor 720, coil antenna system 710 (e.g., referring to FIG. 7B), and electrode system 700 (e.g., referring to FIG. 7A) may correspond to the average properties of the materials flowing through the flowline. Therefore, tomography may be applied to measure inconsistent fluid within flowline 606.

Figure 7D:
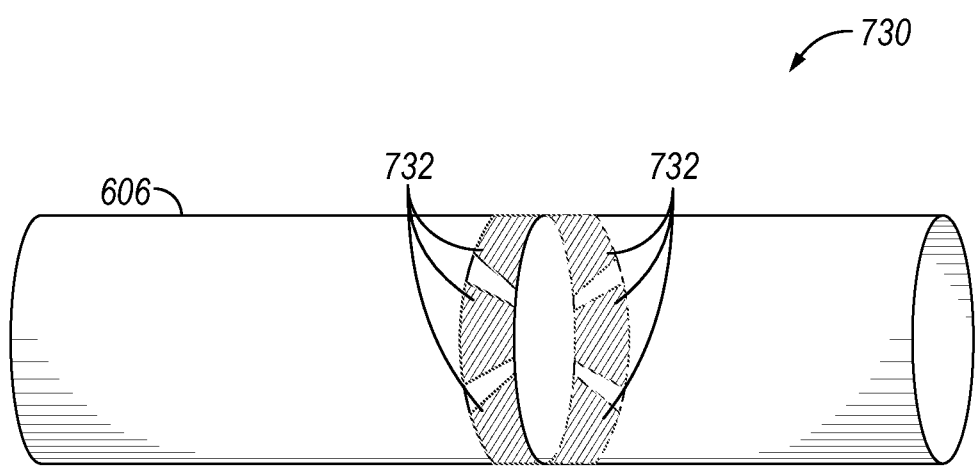
FIG. 7D illustrates electrical impedance tomography system.

FIG. 7D illustrates electrical impedance tomography system 730. One or more electrodes 732 may be displaced around the inner circumference of flowline 606. Each electrode of the one or more electrodes 732 may operate as a transmitter or receiver electrode. Any number of electrodes operate as a transmitter or receiver electrode, with the exception that at least one electrode must be a transmitter and one electrode must be a receiver. A static (DC) or quasi-static (with frequencies less than 100 kHz) current may be injected into transmitter electrodes, and the potential difference between different transmitter-receiver electrode pairs may then be measured. Such measurements may then be converted into conductivity and permittivity images, to be discussed in detail below. Additionally, capacitive plates may be placed along the circumference of the flowline instead of one or more electrodes 732. In such examples, measuring the capacitance between different plates and processing the data, a cross-sectional image of the dielectric permittivity of the material flowing through the flowline may be measured. Conductivity values for materials with low inherent conductivity (i.e., insulators) may also be measured. In further examples, capacitor plates/electrodes are replaced by induction coils. As previously described in coil antenna system 710 (e.g., referring to FIG. 7B) when a coil in the transmitter mode is fired up by passing current through it, a magnetic field is created which induces an electric field. This electric field induces a secondary magnetic field inside a coil in the receiving mode. Thus, the inductance between these two coils may be measured. These measurements may then be repeated for all the remaining coil pairs and converted into conductivity and permeability images. All measurement techniques described in FIGS. 7A-7D may alternatively be replaced with a resonator antenna 160 (e.g., referring to FIG. 6) to be discussed in detail below.

Figure 8A:
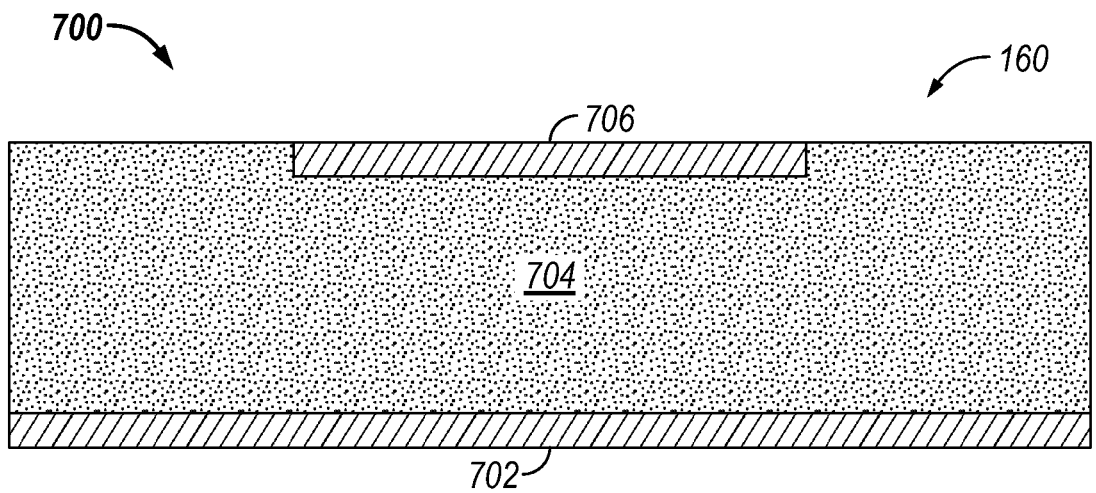
FIG. 8A illustrates a resonator antenna configured as a microstrip patch antenna.

FIG. 8A illustrates resonator antenna 160 configured as a microstrip patch antenna 800. In examples, resonator antenna 160 may operate between 10 MHz to 300 GHz. These high frequencies may be more suitable for imaging applications in oil-based mud environments. However, operation in water-based mud environments may also be possible. As illustrated, a microstrip patch antenna 800 may comprise a metallic ground plane 802, a dielectric substrate 804, and a conductive patch 806 on top of dielectric substrate 804. Therefore, microstrip patch antenna 800 may not be invasive within flowline 606 and as such does not experience coating, in contrast to systems and techniques described above in FIGS. 7A-7D. A reflectometry measurement may be made with microstrip patch antenna 800 by measuring one or more S-parameters (for example, S11 is the reflection coefficient of the signal at the feeding port) for different formations. S-parameters is an acronym for scattering parameters and $S_{ij}$ denote the ratio of the reflected power wave at port i to incident power wave at port j of a circuit while all the ports other than port j are terminated in matched loads. As microstrip patch antenna constitutes a dielectric cavity, they may resonate at a specific frequency (i.e., resonance frequency).

Resonance frequency of microstrip patch antenna 800 is a function of its geometry and the materials forming microstrip patch antenna 800. Resonance frequency is inversely proportional to the size of microstrip patch antenna 800 and the dielectric constant of dielectric substrate 804. Other parameters of the antenna geometry or the properties of the materials, such as the magnetic permeability of dielectric substrate 804, may also be modified in some implementations. Thus, the resonance frequency of a microstrip patch antenna 800 may change by changing one or more properties of microstrip patch antenna 800. Properties may comprise, but are not limited to, a permittivity of the substrate, a permeability of the substrate, a width, a length, and/or a thickness. The magnitude and phase of the reflection coefficient at the feeding port (referred to as S11 parameter) may be affected by the properties of the formation that the electromagnetic waves are being transmitted. As a result, measured S-parameters also vary with the electrical properties of the fluid. Thus, measured S-parameters may be used to estimate the electrical properties of the fluid through techniques such as inversion as discussed below.

In examples, slots (not illustrated) may be cut on conductive patch 806 to facilitate the transmission of electromagnetic waves into the surrounding formation. Multiple slots may be present on conductive patch 806, which may change the operational characteristics of microstrip patch antenna 800. If there are multiple slots, the effective measurement point of microstrip patch antenna 800 may be considered to be the geometric center of the slots. A geometric center is a location after averaging out the position of each slot. However, since characteristics of the formation (and the borehole) immediately in front of each slot may be different, this is only an approximation.

Microstrip patch antenna 800 may be connected to information handling system 122 (e.g., referring to FIG. 1) by microstrip lines, coaxial probes, aperture coupling or proximity coupling. Additionally, photoetching may be used for implementing patch and the feed lines on dielectric substrate 804. A dielectric substrate 804 may be polyvinyl chloride (PVC), High-density polyethylene (HDPE), acrylonitrile butadiene styrene (ABS), polyetheretherketone (PEEK), or ceramic materials such as vitrified clay. While FIG. 8A illustrates resonator antenna 160 as a microstrip patch antenna 800, resonator antennas 160 may be other antennas.

Figure 8B:
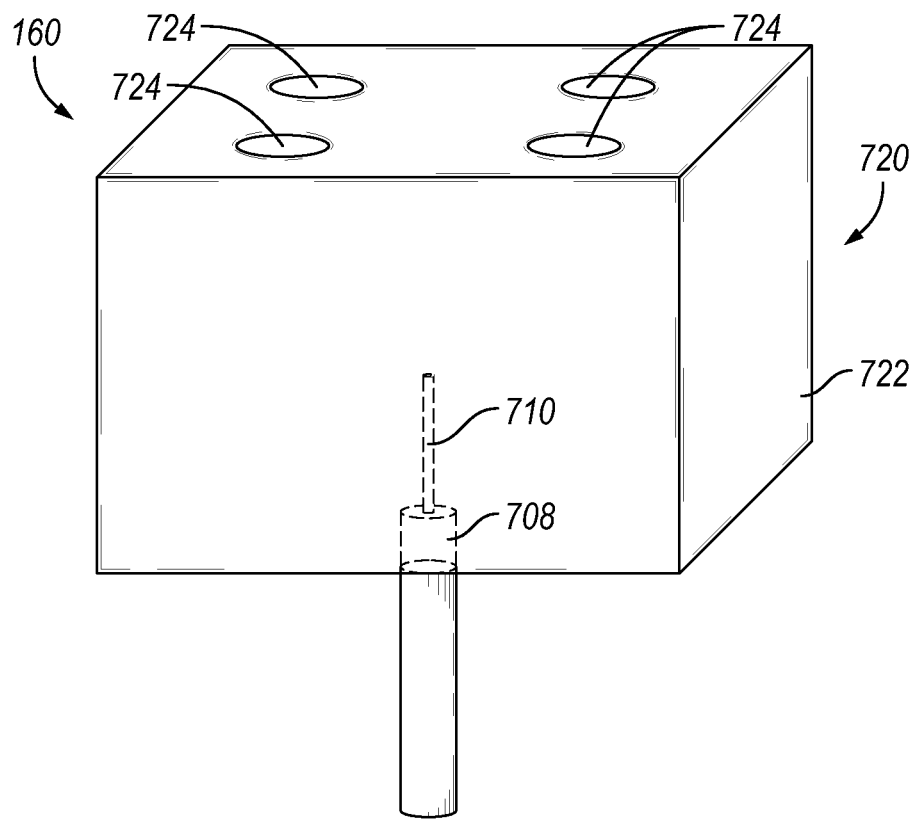
FIG. 8B illustrates the resonator antenna configured as a cavity resonator.

FIG. 8B illustrates resonator antenna 160 configured as a cavity resonator 820. As illustrated, cavity resonator 820 may comprise one or more conducting walls 822 with one or more slots 824. Slots are openings in the conducting wall that provides a path between the outside of the cavity resonator 820 and its inside. As illustrated, conducting walls 822 may further comprise a hole or iris 808, which may feed (i.e., provide power to) cavity resonator 820 and radiating the electromagnetic energy. Cavity resonator 820 may also be referred to as cavity-backed slots. In the cavity-backed slot design, slots 824 may be the only openings on conducting walls 822 surrounding cavity resonator 820. As a result, radiation from cavity resonator 820 may occur and/or originate from each slot 824. Cavity resonator 820 may have a high Q-factor. Q-factor (also referred to as the quality factor) is a measure of the ratio of the energy stored to energy lost in a resonant device and a higher Q-factor represents lower losses. Therefore, cavity resonator 820, may not be invasive within flowline 606 and as such does not experience coating, in contrast to systems and techniques that utilize electrode sensors as described above in FIGS. 7A and 7D. In the example of resonator antenna 160 in direct contact with the fluid and is subject to coating, the resulting effect on performance is negligible since the resonator antenna 160 do not require a direct conduction path as needed for the electrode sensors working based on Galvanic principles. Furthermore, resonator antennas 160 do not require non-conductive or non-magnetic flowlines in contrast to systems and techniques described above in FIG. 7B utilizing coil sensors or purpose built flowlines in contrast to systems and techniques described above in FIG. 7C utilizing waveguide flowline sensor. As with the microstrip patch antenna, as the dimensions of cavity resonator 820 and the dielectric constant of the material filling the inner cavity of cavity resonator 820) and slots 824 increases, the resonance frequency decreases. Thus, the resonance frequency of cavity resonator 820 may change by changing one or more properties of cavity resonator 820. Properties may comprise, but are not limited to, a permittivity of the substrate, a permeability of the substrate, a width, a length, and/or a thickness. Such a resonator may also be fed through a feeding port or a waveguide 810 connected to a hole or iris 808 on the wall of slot 824. Filling slots 824 with different material of different dielectric constants may allow for cavity resonator 820) to resonate at different frequencies. Cavity resonator 820 may be connected to information handling system 122 by microstrip lines, coaxial probes, aperture coupling or proximity coupling. Both microstrip patch antenna 800 and cavity resonator 820 are implementations of resonator antenna 160 and may be used on downhole fluid sampling tool 100 in downhole operations to take one or more measurements of a fluid moving through flowline 606 (e.g., referring to FIG. 6).

Figure 9:
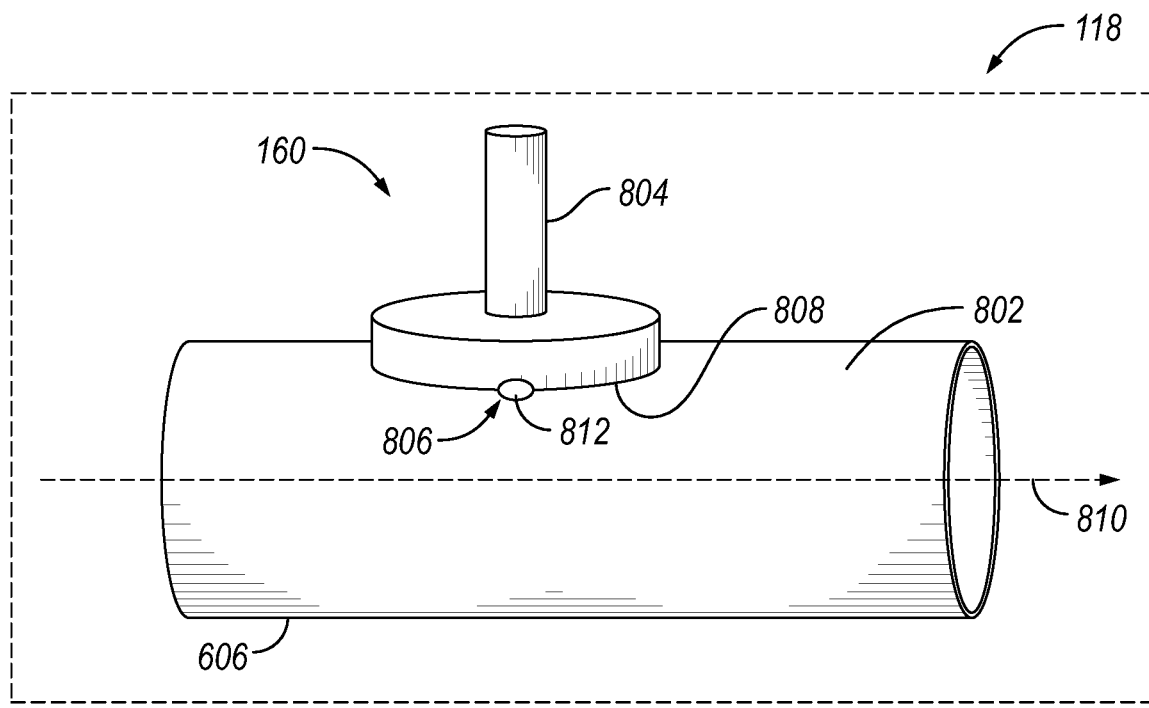
FIG. 9 illustrates the fluid analysis module that comprises the resonator antenna disposed between the outer surface and the inner surface of the flowline.

FIG. 9 illustrates fluid analysis module 118 that comprises a resonator antenna 160) disposed along an outer surface 902 of flowline 606. As depicted in FIG. 9, resonator antenna 160 may be a cavity resonator 820 (e.g., referring to FIG. 8) as described above. An electrical connection 904 may deliver power and/or commands from information handling system 122 to resonator antenna 160. Herein, a flowline 606 may be connected to resonator antenna 160 via coaxial cables. As such, resonator antenna 160) may comprise a slot 906 disposed on an exterior surface 908 of resonator antenna 160. In examples, slot 906 may match with a slot cut 912 on outer surface 902 of flowline 606. Slot 906 and cut slot 912 may be filled with a dielectric material to ensure the sealing of fluid 910 inside flowline 606. A dielectric material as previously described, may be polyvinyl chloride (PVC), High-density polyethylene (HDPE), acrylonitrile butadiene styrene (ABS), polyetheretherketone (PEEK), or ceramic materials such as vitrified clay. In examples, flowline 606 may be formed from nonconducting material. Thus, a slot cut 912 may not be utilized on outer surface 902 of flowline 606 as nonconducting material may allow for transmission of electromagnetic waves through flowline 606. Therefore, resonator antenna 160) may not be invasive within flowline 606 and as such does not experience coating, in contrast to systems and techniques described above in FIGS. 7A and 7D utilizing electrode sensors. Furthermore, they do not require non-conductive or non-magnetic flowlines in contrast to systems and techniques described above in FIG. 7B utilizing coil sensors or purpose-built flowlines in contrast to systems and techniques described above in FIG. 7C utilizing waveguide flowline sensor.

During measurement operations, resonator antenna 160 may transmit an electromagnetic (EM) wave into flowline 606 and receive a reflected EM wave from flowline 606. With the transmitted EM wave and the reflected EM wave, resonator antenna 160 may calculate a S11 parameter of fluid 910 inside flowline 606. Herein, S11 parameter is calculated as the ratio of the reflected power wave from the $1^{st}$ port to an incident power wave at the $1^{st}$ port. Thus, S11 measures the reflection of transmitted power back to the antenna. From a calculated S11 parameter, fluid properties may be estimated. For example, S11 parameter is a function of the reflection coefficient of the fluid, which in turn depends on electrical properties of the fluid such as the dielectric permittivity, conductivity and permeability. In examples, resonator antenna 160 may be disposed within fluid analysis module 118 in any suitable configuration for measurement operations.

Figure 10:
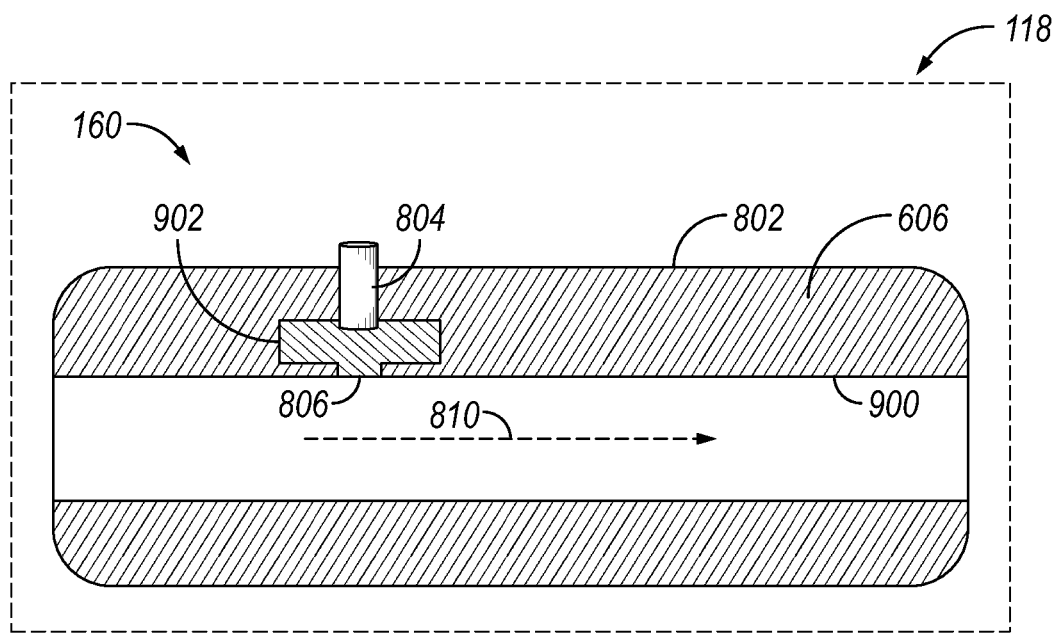
FIG. 10 illustrates fluid analysis module that comprises a resonator antenna disposed between outer surface and inner surface.

FIG. 10 illustrates fluid analysis module 118 that comprises a resonator antenna 160 disposed between outer surface 902 and inner surface 1000 of flowline 606. If the material filling the volume between the inner surface 1000 and the outer surface 902 of flowline 606 is conductive, resonator antenna 160 may be disposed within indent 1002. If the material filling the volume between the inner surface 1000 and the outer surface 902 of flowline 606 is nonconductive, indent 1002 may be carved out and covered with conducting material except for slot 906, which may enable transmission of electromagnetic (EM) waves (i.e., radiation) into flowline 606. Slot 906 may be covered with a dielectric material to prevent fluid 910 from entering indent 1002. Therefore, resonator antenna 160 may not be invasive within flowline 606 and as such does not experience coating, in contrast to systems and techniques described above in FIGS. 7A and 7D. An electrical connection 904 may deliver power and/or commands from information handling system 122 to resonator antenna 160. The S11 parameter may be measured and used to determine the properties of fluid 910 inside flowline 606, as previously described. It should be noted that S11 parameters are discussed above, other properties and/or parameters may also be measured.

During measurement operations a complex permittivity of fluid 910 from one or more S-parameter measurements may be formed. This process may be based on a numerical forward model of resonator antenna 160 inside flowline 606, which is created and processed on information handling system 122 (e.g., referring to FIG. 1). Numerical forward models implemented herein may be Finite Difference Time Domain (FDTD), FEM (Finite Element Method) and MoM (Method of Moments). However additional numerical forward models may be used. S-parameter measurements taken by resonator antenna 160 may be compared with the response of the forward model for different fluid properties to determine the property whose response best matches the actual measurements. The responses of the forward model may have been computed beforehand and stored in a library. A response that produces the lowest misfit (in the least squares sense) to the actual response among the responses in the library may be selected. In other examples, an iterative inversion algorithm may be used to determine complex permittivity of fluid 910. An iterative inversion algorithm may run the numerical forward model at each step or may use precomputed responses (i.e., an interpolation may be employed to determine the responses for points that do not exactly lie within the precomputed library).

Software packages run on information handling system 122 perform optimization/inversion tasks are commonly available in programming languages used in scientific computation. The goal of the inversion may be to minimize a misfit function as illustrated in Equation (1):

$$\arg_{\overline{X}} \min \left\| \overline{S}^{Meas} - \overline{S}^{Model}(\overline{X}) \right\| \quad (1)$$

In Equation (1), $\overline{S}^{Meas}$ denotes the measurements from resonator antenna 160 while $\overline{S}^{Model}$ denotes the modelling outputs. $\overline{X}$ is the parameters of the numerical forward model (i.e., formation parameters that are desired to be found.) Overbars indicate these quantities may be vectors or matrices, which may also be represented as vectors after a flattening operation. In examples, additional regularization terms may be added to utilize priori information to ensure smoothness of results. Generally, Equation (1) may be utilized for a single resonator antenna 160. Additionally, there may be multiple resonance frequencies (or a band of frequencies) of a single resonator antenna 160. However, it may not be feasible to tune multiple frequencies from a single resonator antenna 160. Therefore, multiple nested resonator antennas 160 may be utilized to perform multi frequency measurements.

Figure 11A:
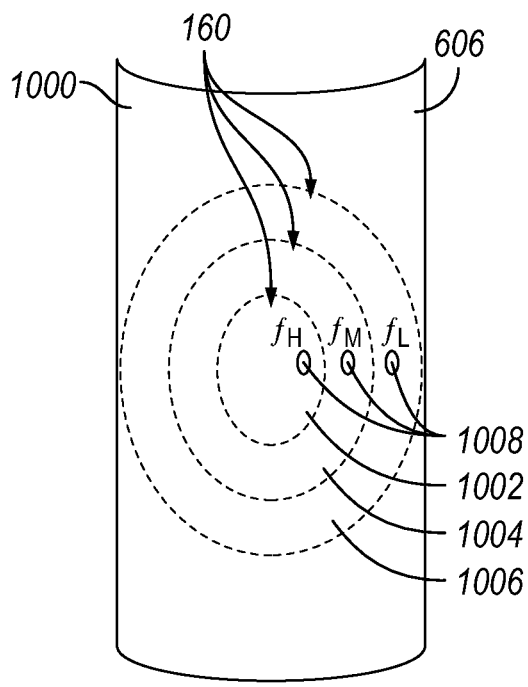
FIG. 11A illustrates an alignment of slots.
Figure 11B:
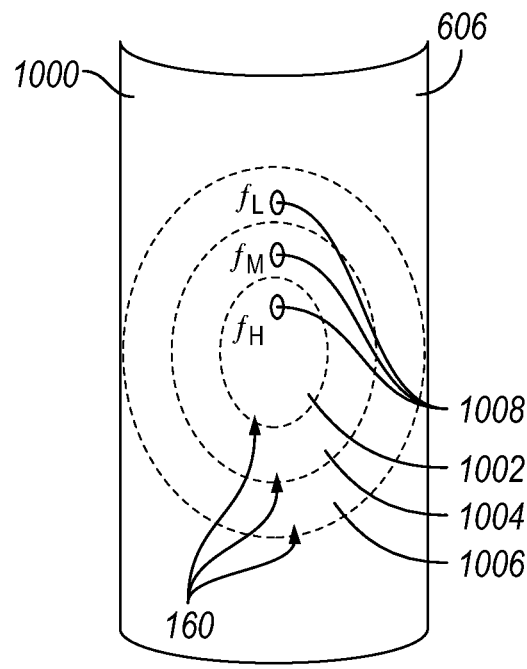
FIG. 11B illustrates another alignment of slots.
Figure 11C:
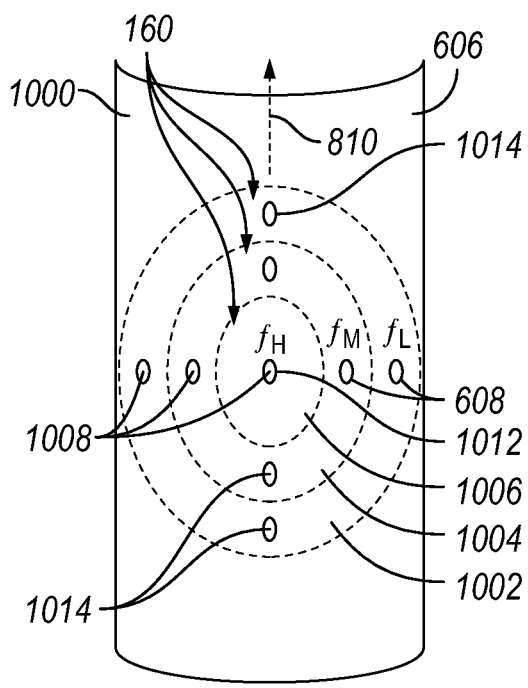
FIG. 11C illustrates another example of alignment of slots.

FIGS. 11A-11C illustrate fluid analysis module 118 that comprise a plurality of resonator antennas 160 disposed along outer surface 902 of flowline 606 or between outer surface 902 and inner surface 1000 of flowline 606. As depicted in FIGS. 11A-11C, resonator antennas 160 may be cavity resonators 820 (e.g., referring to FIG. 8A). In order to make multi frequency measurements at substantially similar locations at different frequencies, several different arrangements may be created. For FIGS. 11A-11C, the face of resonator antennas 160 are shown to be circular, but they may be any other shape, such as an ellipse, rectangle or a square. Similarly, although they are shown to be concentric, their centers may not coincide. Additionally, there may be a plurality of resonator antennas 160 in proximity to one another but not nested. The resonance frequency of resonator antennas 160 may be inversely proportional to their physical sizes. Thus, smallest resonator antenna 1102 (innermost cavity) may resonate at a higher frequency $f_H$, second largest resonator antenna 1104 may resonate at a middle frequency $f_M$, and largest resonator antenna 1106 may resonate at a lower frequency $f_L$. Slot 906 may be opened on each resonator antenna 160) to enable the radiation of the electromagnetic waves, as discussed above. Slot 906 of each resonator antenna 160 may be located at the same axial position. Slot 906 may be located close to each other, and the measurements may be assumed to be performed at the same azimuthal position for different frequencies. There may be multiple such nested antenna structures on flowline 606. Although there are three groups of resonator antennas 160 (operating at three different frequencies) in this example, there may be any number of nested resonator antennas 160) in other implementations which may enable measurements at different number of frequencies.

An implementation of slots 906 on the same azimuthal position is depicted in FIG. 11A. In this alignment, there exist three resonator antenna 160 aligned perpendicular to flowline 606. FIG. 11B illustrates another alignment of slots 906 for resonator antennas 160 that are aligned parallel to flowline 606. Similar to FIG. 11A, slots 906 of each nested resonator antenna 160) arrangement may be located at close proximity to each other and may be assumed to be at the same axial position during processing. Measurements from one or more slots 906 are interpolated and aligned to the same depth. FIG. 11A illustrates slots 1108 aligned in a horizontal direction. FIG. 11B illustrates slots 1108 aligned in the vertical direction. In these alignments of slots 906 for FIG. 11A and FIG. 11B, only a single slot 1108 has been depicted for each resonator antenna 160. It may be possible to have multiple slots 1108 in other arrangement schemes. For example, FIG. 11C illustrates largest resonator antenna 1106 and second largest resonator antenna 1104 each having four slots 1108.

Slots 1108 may be arranged in a symmetric manner such that their geometric center (e.g., the average of the positions of slots 1108) lies on the same location as a single slot 1112 located in smallest resonator antenna 1102. As a result, the measurement point of four outer sensors 1114 may be the same as smallest resonator antenna 1102. However, the separation between one or more single slots 1112 and two outer sensors 1114 in this example may decrease the resolution of measurements taken during measurement operations. Measurements taken by resonator antennas 160 may provide S11 parameters for smallest resonator antenna 1102, second largest resonator antenna 1104, and largest resonator antenna 1106. As previously described, implementations of cavity resonators 820 (e.g., referring to FIG. 8B) configured as resonator antenna 160 may measure S11 parameters of fluid 910 inside flowline 606. In examples, smallest resonator antenna 1102 (innermost cavity) may resonate at a higher frequency $f_H$, second largest resonator antenna 1104 may resonate at a middle frequency $f_M$, and largest resonator antenna 1106 may resonate at a lower frequency $f_L$. Resonator antennas may be performed to measure nested S21 parameters, to be discussed below.

Figure 12A:
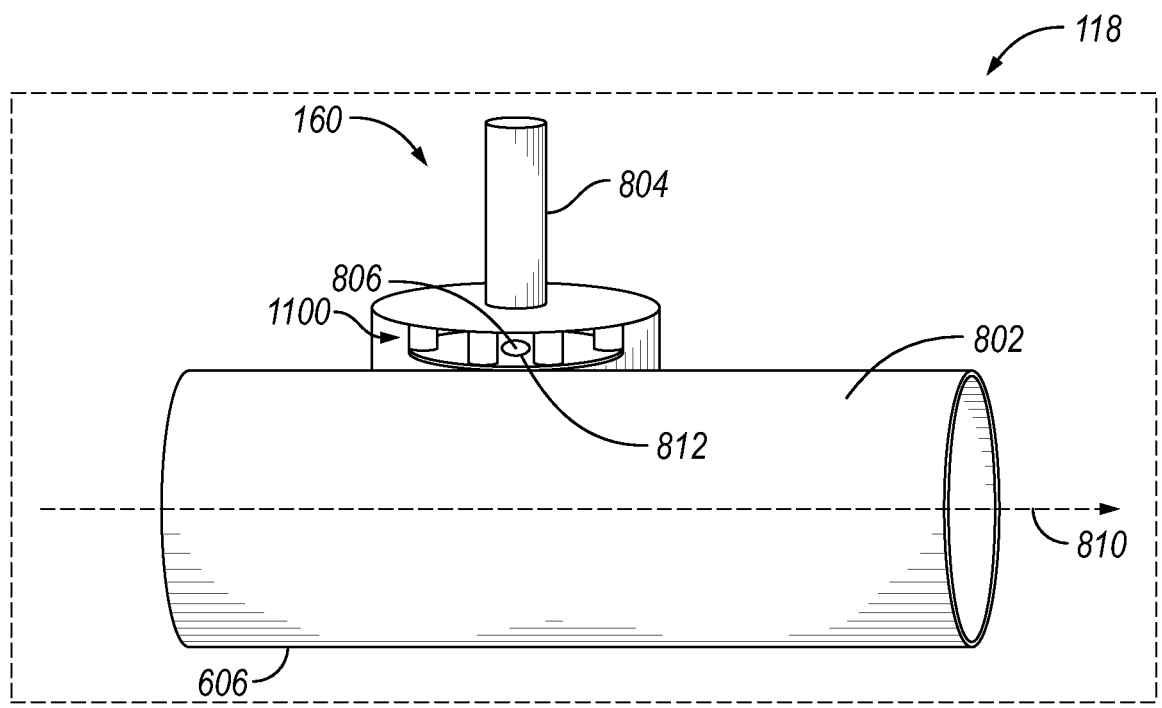
FIG. 12A illustrates the fluid analysis module that comprises the resonator antenna as a microstrip patch antenna disposed along the outer surface of the flowline.

FIG. 12A illustrates fluid analysis module 118 that comprises a resonator antenna 160 configured to be a microstrip patch antenna 800 (e.g., referring to FIG. 8A) disposed along an outer surface 902 of flowline 606. As depicted in FIG. 12A, resonator antenna 160 may be a microstrip patch antenna, as described above. An electrical connection 904 may deliver power and/or commands from information handling system 122 (e.g., referring to FIG. 1) to resonator antenna 160). As such, resonator antenna 160 may comprise a slot 906 on its outside may be matched with a slot cut 912 on the outer surface of flowline 606, similar to a cavity resonator. Slot 906 and slot cut 912 may be filled with dielectric material, as described above to ensure the sealing of the fluid inside flowline 606. In examples, if flowline 606 is formed out of nonconducting material, there may not be a need a slot cut 912 on the outer surface of flowline 606 since nonconducting material may allow the transmission of the electromagnetic waves. Additionally, resonator antenna 160 may comprise conducting vias 1200 to reduce the radiation loss from microstrip patch antenna 800 (e.g., referring to FIG. 8A). Resonator antenna 160 may transmit an electromagnetic (EM) wave into flowline 606 and receive a reflected EM wave from flowline 606. With the transmitted EM wave and the reflected EM wave, resonator antenna 160 may calculate the S11 parameter of fluid 910 inside flowline 606. In FIG. 12A, a microstrip patch antenna 800 (e.g., referring to FIG. 8B) is disposed on the outside of flowline 606. However, further embodiments may also include a microstrip patch antenna 800 disposed within flowline 606. Microstrip patch antenna may also be located in between the outer surface and the inner surface of the flowline. As previously depicted for cavity resonators, an indent may be cut within the flowline wall in the location of the antenna. In the case of a non-conducting flowline, conducting vias may again be used to improve the radiation efficiency of this design.

Figure 12B:
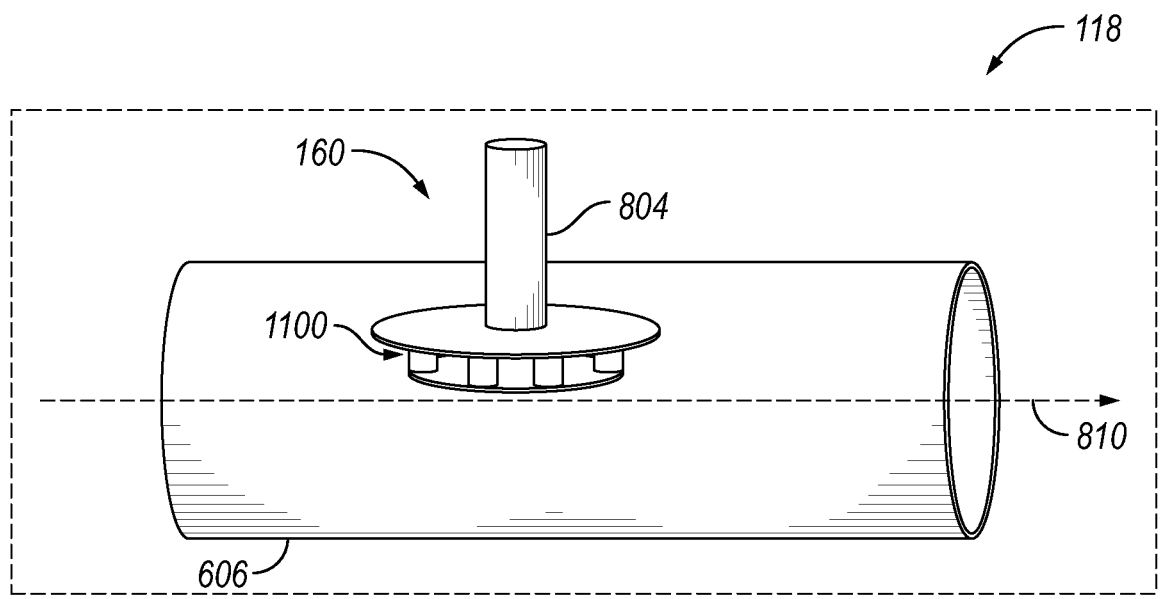
FIG. 12B illustrates the fluid analysis module that comprises the resonator antenna disposed within the flowline.

FIG. 12B illustrates fluid analysis module 118 that comprises a resonator antenna 160) disposed within flowline 606. As depicted in FIG. 12B, resonator antenna 160 may be a microstrip patch antenna 800 (e.g., referring to FIG. 8A). In examples, fluids may pass through the resonator antenna 160. Thus, the fluid may act as the substrate of microstrip patch antenna 800. Thus, properties of the fluid may affect the radiation characteristics (and thus, the S parameters) of resonator antenna 160. This quantity may be measured and processed to determine electrical properties of the fluid. Additionally, conducting vias 1200 may form a measurement volume 1204. In other implementations, resonator antenna may be a cavity resonator. Cavity resonators may impede the fluid flow more than a microstrip patch antenna.

Aligning at least two of the slots with the direction of the fluid flow may alleviate this issue to an extent. Resonator antenna 160 disposed within flowline 606 may transmit an electromagnetic (EM) wave into measurement volume 1204 and receive a reflected EM wave from measurement volume 1204. With the transmitted EM wave and the reflected EM wave, resonator antenna may calculate an S11 parameter within measurement volume 1204. Although resonator antenna designs depicted in FIG. 12A and FIG. 12B are invasive and thus may be subject to coating, the effect on the performance of the antenna may be minimal since the resonator antennas do not require a direct conduction path unlike system and techniques shown in FIG. 7A and FIG. 7D utilizing electrode sensors. Furthermore, they do not require non-conductive or non-magnetic flowlines in contrast to systems and techniques described above in FIG. 7B utilizing coil sensors or purpose-built flowlines in contrast to systems and techniques described above in FIG. 7C utilizing waveguide flowline sensor. Methods and systems discussed above may calculate an S11 parameter of the resonator antenna that varies with the fluid 910 properties inside flowline 606. Additionally, methods and systems may solve for multiphase tomography with S11 parameters.

Fluid inside flowline 606 may comprise multiple phases. Specifically, one or more fluids and gases may flow through the flowline 606 at the same time. As previously described multiple nested resonator antennas 160 implementation may transmit multiple frequencies. Measurements taken by one or more resonator antennas 160 may be used to identify different components from each other. However, calculations may be based on assumptions about the distribution of the components inside flowline 606. Therefore, resolving multiphase flow may be based on tomography. A tomography technique that utilizes resonator antennas 160 may be resistant to corrosion, operate with both conductive and nonconductive flowlines, and be low profile and easy to manufacture.

Figure 13C:
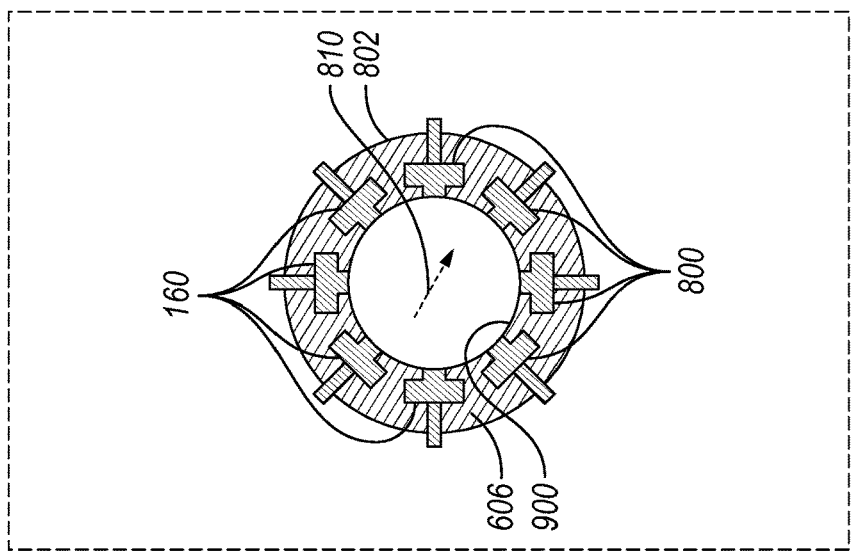
FIG. 13C illustrates an example of resonator antennas as cavity resonators inside the outer wall of the flowline.
Figure 13B:
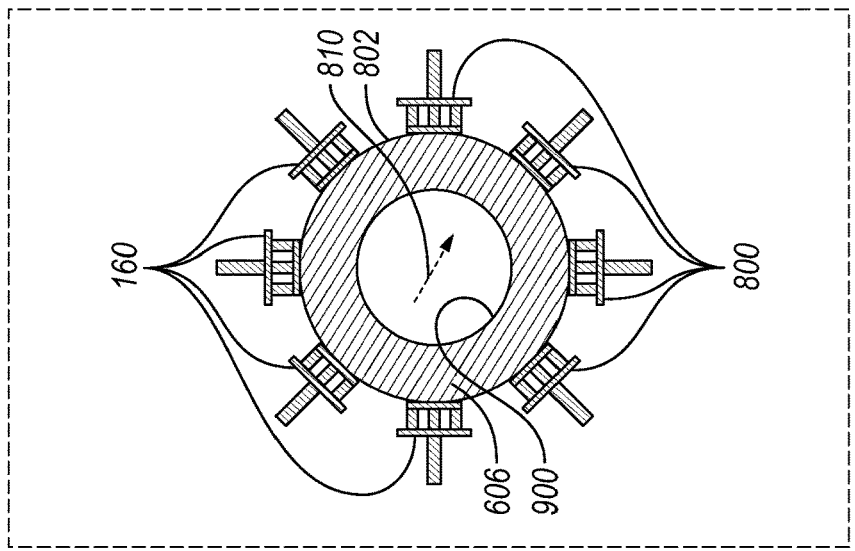
FIG. 13B illustrates the resonator antennas as microstrip patch antennas located outside the flowline.
Figure 13A:
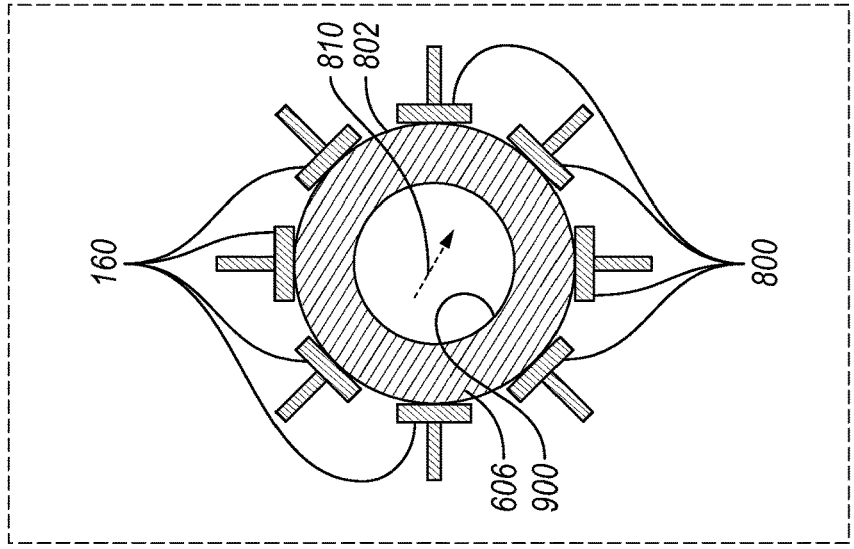
FIG. 13A illustrates the resonator antennas as cavity resonators located outside the flowline.

Tomography techniques may use resonator antennas 160 configured as microstrip patch antennas 800 (e.g., referring to FIG. 8A) and cavity resonator (e.g., referring to FIG. 8B). FIG. 13A illustrates resonator antennas 160 as cavity resonators 820 located outside flowline 606. Similarity, FIG. 13B illustrates resonator antennas 160 as microstrip patch antennas 800 disposed outside flowline 606. FIG. 13C illustrates cavity resonators 820 disposed inside the outer surface 902 of flowline 606 (e.g., referring to FIG. 8). Although a total of eight resonator antennas 160 have been illustrated in FIGS. 13A-13C, the actual number of resonator antennas 160 may be less or more than this number. In the tomography applications, an S21 parameter between a pair of resonator antennas 160 may be measured by using one resonator antenna 160 as a transmitter and one resonator antenna 160 as a receiver. Herein, resonator antenna 160 which transmits an electromagnetic (EM) wave may be identified as the transmitting antenna, while a receiving antenna may be the resonator antenna 160 which receives a reflected (EM) wave. The S21 parameter is dependent on the medium in between the transmitting antenna and the receiving antenna (i.e., of fluid 910 inside flowline 606). In general, the Sji parameter is the element of the scattering matrix, that is calculated as the ratio of the power wave received at the $j^{th}$ port due to an incident power wave at the $i^{th}$ port (when the $j^{th}$ port is terminated in a matched load). Herein, S21 is denoted as the forward voltage gain and is a measure of the transmission of the power between the two ports. It is possible to incorporate the S11 parameter in addition to the S21 parameter in an inversion for a tomography application to further improve the amount of information available and thus increase the accuracy of the tomography.

An EM wave transmitted by a transmitting antenna may be received as by any resonator antenna 160 within one embodiment. Therefore, the number of measurable S21 parameter for every resonator antenna 160 may be one less than the total number of resonator antennas 160 in the embodiment. By measuring the S21 parameters between different resonator antenna 160 pairs, a tomographic image of the volume inside the flowline may be obtained. The tomographic image may be obtained by traditional methods such as the Fourier inversion theorem (e.g., the Radon transform) using at least one S21 parameter between at least one resonator antenna 160 pairs. The tomographic image (or the measurement data used in obtaining the tomographic image) may be inverted to produce resistivity and permittivity images of the flowline as described in the previous section. Furthermore, nested resonator antennas 160 may be used with different operating frequencies in a tomography application, as described above. With nested resonator antennas 160, a different tomographic image may be obtained for each frequency which may be used to resolve dispersion characteristics of the multiphase fluids.

Currently technology is not able to provide an antenna structure for traditional flowlines that does not degrade over time due to the accumulation of contaminants from the fluids and capable of making measurements in conducting flowlines. Systems and methods herein relate to resonator antennas for performing resistivity and permittivity measurements in flowlines. Resonator antennas may not be affected by the accumulation of particles and may measure both conductive and nonconductive fluid. Additionally, improvements over current technology reside in tomography measurements with a wide range of possible configurations.

Statement 1: A downhole fluid sampling tool may comprise one or more probes configured to extend into a formation, a pump configured to collect a fluid from the formation through the one or more probes, a flowline configured to transport the fluid from the formation through the one or more probes and through the downhole fluid sampling tool, and a fluid analysis module comprising a resonator antenna disposed on the flowline and configured to measure at least one property of the fluid.

Statement 2: The downhole fluid sampling tool of statement 1, wherein the resonator antenna is a cavity resonator.

Statement 3: The downhole fluid sampling tool of statement 2, wherein the cavity resonator is disposed on an outer surface of the flowline.

Statement 4: The downhole fluid sampling tool of statement 2, wherein the cavity resonator is disposed within the flowline and the fluid inside the flowline acts as a substrate of a cavity resonator.

Statement 5: The downhole fluid sampling tool of statements 2-4, wherein the cavity resonator comprises a slot.

Statement 6: The downhole fluid sampling tool of statement 5, wherein the flowline comprises a cut slot that is aligned with the slot from the cavity resonator and filled with dielectric material.

Statement 7: The downhole fluid sampling tool of statement 6, wherein the cavity resonator is configured to: transmit an electromagnetic (EM) wave through the slot and cut slot and into the flowline, and measure a reflected EM wave through the slot and cut slot from the flowline and compute an S11 parameter indicative of electrical properties of the fluid.

Statement 8: The downhole fluid sampling tool of statement 2, wherein the cavity resonator is disposed within at least part of a cavity carved within a wall of the flowline.

Statement 9: The downhole fluid sampling tool of statements 1-8, wherein the resonator antenna comprises two or more nested resonator antennas configured to measure a plurality of S11 parameters at more than one frequency.

Statement 10: The downhole fluid sampling tool of statement 1, wherein the resonator antenna is a microstrip patch antenna.

Statement 11: The downhole fluid sampling tool of statement 10, wherein the microstrip patch antenna comprises a slot and the flowline comprises a cut slot that is aligned with the slot from the microstrip patch antenna and filled with dielectric material.

Statement 11: The downhole fluid sampling tool of statement 10, wherein the microstrip patch antenna comprises a slot and the flowline comprises a cut slot that is aligned with the slot from the microstrip patch antenna and filled with dielectric material.

Statement 12: The downhole fluid sampling tool of statement 11, wherein the microstrip patch antenna is disposed within the flowline and the fluid inside the flowline acts as a substrate of the microstrip patch antenna.

Statement 13: The downhole fluid sampling tool of statements 11 or 12, wherein the microstrip patch antenna comprises conducting vias located around a dielectric material.

Statement 14: The downhole fluid sampling tool of statement 11, wherein the microstrip patch antenna is disposed on an outer surface of the flowline.

Statement 15: The downhole fluid sampling tool of statement 11, wherein the microstrip patch antenna is disposed between an inner surface of the flowline and an outer surface of the flowline.

Statement 16: A method may comprise disposing a downhole sampling tool into a formation, extending one or more probes from the downhole sampling tool into the formation, collecting a fluid from the formation through the one or more probes with a pump, transporting the fluid from the formation through the one or more probes and through the downhole fluid sampling tool with a flowline, and measuring at least one property of the fluid with two or more resonator antennas that are disposed on or within an outer surface of the flowline.

Statement 17: The method of statement 16, further comprising measuring at least one S21 parameter with the two or more resonator antennas.

Statement 18: The method of statement 17, wherein the two or more resonator antennas are nested and configured to measure a plurality of S21 parameters at more than one frequency.

Statement 19: The method of statement 18, further comprising forming a resistivity image and permittivity image from at least one S21 parameter.

Statement 20: The method of statement 19, wherein at least one property of the fluid is identified with at least the resistivity image and the permittivity image using tomographic techniques.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A downhole fluid sampling tool comprising:
one or more probes configured to extend into a formation;
a pump configured to collect a fluid from the formation through the one or more probes;
a flowline configured to transport the fluid from the formation through the one or more probes and through the downhole fluid sampling tool; and
a fluid analysis module comprising two or more nested resonator antennas disposed on the flowline and configured to measure at least one property of the fluid, wherein one nested resonator antenna is disposed within the bounds of another nested resonator antenna and the boundaries of each of the two or more nested resonator antennas are different.

2. The downhole fluid sampling tool of claim 1, wherein the resonator antenna is a cavity resonator.

3. The downhole fluid sampling tool of claim 2, wherein the cavity resonator is disposed on an outer surface of the flowline.

4. The downhole fluid sampling tool of claim 2, wherein the cavity resonator is disposed within the flowline and the fluid inside the flowline acts as a substrate of a cavity resonator.

5. The downhole fluid sampling tool of claim 2, wherein the cavity resonator comprises a slot.

6. The downhole fluid sampling tool of claim 5, wherein the flowline comprises a cut slot that is aligned with the slot from the cavity resonator and filled with dielectric material.

7. The downhole fluid sampling tool of claim 6, wherein the cavity resonator is configured to:
transmit an electromagnetic (EM) wave through the slot and cut slot and into the flowline; and
measure a reflected EM wave through the slot and cut slot from the flowline and compute an S11 parameter, wherein the S11 parameter is a function of a reflection coefficient of the fluid.

8. The downhole fluid sampling tool of claim 2, wherein the cavity resonator is disposed within at least part of a cavity carved within a wall of the flowline.

9. The downhole fluid sampling tool of claim 1, wherein the resonator antenna comprises the two or more nested resonator antennas configured to measure a plurality of S11 parameters at more than one frequency, wherein the S11 parameters are a function of a reflection coefficient of the fluid.

10. The downhole fluid sampling tool of claim 1, wherein the resonator antenna is a microstrip patch antenna.

11. The downhole fluid sampling tool of claim 10, wherein the microstrip patch antenna comprises a slot and the flowline comprises a cut slot that is aligned with the slot from the microstrip patch antenna and filled with dielectric material.

12. The downhole fluid sampling tool of claim 11, wherein the microstrip patch antenna is disposed within the flowline and the fluid inside the flowline acts as a substrate of the microstrip patch antenna.

13. The downhole fluid sampling tool of claim 11, wherein the microstrip patch antenna comprises conducting vias located around a dielectric material.

14. The downhole fluid sampling tool of claim 11, wherein the microstrip patch antenna is disposed on an outer surface of the flowline.

15. The downhole fluid sampling tool of claim 11, wherein the microstrip patch antenna is disposed between an inner surface of the flowline and an outer surface of the flowline.

16. A method comprising:
disposing a downhole sampling tool into a formation;
extending one or more probes from the downhole sampling tool into the formation;
collecting a fluid from the formation through the one or more probes with a pump;
transporting the fluid from the formation through the one or more probes and through the downhole fluid sampling tool with a flowline; and
measuring at least one property of the fluid with two or more resonator antennas that are disposed on or within an outer surface of the flowline and the boundaries of each of the two or more nested resonator antennas are different, wherein the at least one property comprises at least one S11 parameter, wherein the S11 parameter is a function of a reflection coefficient of the fluid.

17. The method of claim 16, further comprising measuring at least one S21 parameter with the two or more resonator antennas, wherein the S21 parameter is a forward voltage gain and is a measurement of power transmissions between the two resonator antennas.

18. The method of claim 17, wherein the two or more resonator antennas are nested and configured to measure a plurality of S21 parameters at more than one frequency.

19. The method of claim 17, further comprising forming a resistivity image and a permittivity image from at least one S21 parameter.

20. The method of claim 19, wherein at least one property of the fluid is identified with at least the resistivity image and the permittivity image using tomographic techniques.

* * * * *